United States Patent [19]

Rooney et al.

[11] 4,112,112
[45] Sep. 5, 1978

[54] PYRROLO[2,1-B] [3]BENZAZEPINES USEFUL FOR PRODUCING A SKELETAL MUSCLE RELAXING OR TRANQUILIZING EFFECT

[75] Inventors: Clarence Stanley Rooney, Worcester, Pa.; Joshua Rokach, Laval; Joseph George Atkinson, Montreal, both of Canada

[73] Assignee: Merck & Co., Inc., Rahway, N.J.

[21] Appl. No.: 803,481

[22] Filed: Jun. 6, 1977

Related U.S. Application Data

[63] Continuation-in-part of Ser. No. 701,001, Jun. 29, 1976, abandoned, which is a continuation-in-part of Ser. No. 592,436, Jul. 2, 1975, abandoned.

[51] Int. Cl.$^2$ .................... C07D 487/04; A61K 31/40
[52] U.S. Cl. ................................. 424/274; 542/471; 544/142; 260/326.31; 260/293.61; 260/326.5 B; 260/326.9; 260/326.5 S; 260/326.62; 424/267; 424/248.56
[58] Field of Search ............... 260/326.9, 326.5 S, 260/326.5 B, 326.25, 326.62, 293.61, 326.31; 542/405, 471; 544/142, 143, 144; 424/267, 274, 248.56

[56] References Cited

U.S. PATENT DOCUMENTS

| | | | |
|---|---|---|---|
| 2,951,082 | 8/1960 | Sprague et al. | 260/328 |
| 3,014,911 | 12/1961 | Engelhardt | 260/293 |
| 3,428,677 | 2/1969 | Engelhardt et al. | 260/556 |
| 3,428,735 | 2/1969 | Engelhardt | 424/330 |
| 3,454,643 | 7/1969 | Cope et al. | 260/570.8 |
| 3,499,037 | 3/1970 | Engelhardt | 260/590 |
| 3,732,212 | 5/1973 | Carabateas | 260/239.3 T |
| 4,029,672 | 6/1977 | Effland et al. | 260/326.5 B |
| 4,056,536 | 11/1977 | Atkinson et al. | 260/326.5 B |
| 4,075,225 | 2/1978 | Rokach et al. | 260/326.31 |

OTHER PUBLICATIONS

Huigsen et al., Chem. Ber., 93, 65–81 (1960).
Weinstein et al., J. Org. Chem., 41, No. 5, 875–878 (1976).

*Primary Examiner*—Paul M. Coughlan, Jr.
*Assistant Examiner*—Diana G. Rivers
*Attorney, Agent, or Firm*—William H. Nicholson; Harry E. Westlake, Jr.

[57] ABSTRACT

11-Aminopropylidene-Pyrrolo[2,1-b] [3]benzazepines are disclosed to have pharmaceutical utility as skeletal muscle relaxants and tranquilizers. They are prepared by a Grignard reaction on pyrrolo[2,1-b] [3]benzazapin-11-ones followed by dehydration, or by a Wittig reaction on the same ketones.

16 Claims, No Drawings

PYRROLO[2,1-b] [3]BENZAZEPINES USEFUL FOR PRODUCING A SKELETAL MUSCLE RELAXING OR TRANQUILIZING EFFECT

RELATIONSHIP TO OTHER APPLICATIONS

This application is a continuation-in-part of copending application Ser. No. 701,001, now abandoned filed June 29, 1976 which in turn is a continuation-in-part of application Ser. No. 592,436, filed July 2, 1975, now abandoned.

BACKGROUND OF THE INVENTION

Over the past several years several so-called tricyclic compounds such as amitriptyline, cyclobenzaprine, nortriptyline and protriptyline have gained importance as centrally acting pharmacological agents. Now with the present invention, there is provided new tricyclic compounds which have skeletal muscle relaxant and tranquilizer activity.

Thus, it is an object of the present invention to provide compounds of structural formula:

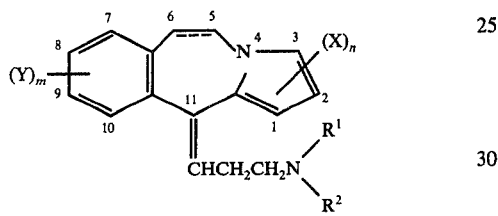

It is a further object to provide processes for the preparation of the compounds; to provide pharmaceutical compositions comprising such compounds; and to provide methods of treatment comprising administering such compounds and compositions when a muscle relaxant and/or tranquilizing effect is indicated.

DETAILED DESCRIPTION OF THE INVENTION

The compounds of the present invention may be represented by the following structural formula:

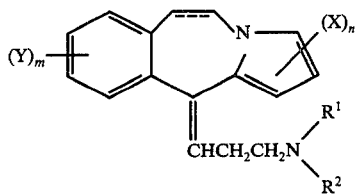

or pharmaceutically acceptable salt thereof, wherein
  the dotted line between positions 5 and 6 represents saturation or unsaturation;
  $n = 3, 2, 1,$ or $0$ (X is hydrogen);
  $m = 4, 3, 2, 1,$ or $0$ (Y is hydrogen);
  X and Y are independently selected from
   (1) hydrogen,
   (2) halo, such as chloro, bromo, fluoro, or iodo,
   (3) formyl,
   (4) lower alkanoyl, especially $C_{2-6}$ alkanoyl such as acetyl, pentanoyl, or 2-methylpropanoyl,
   (5) lower alkyl, expecially $C_{1-5}$ alkyl, either straight or branched chain, such as methyl, propyl, or pentyl,
   (6) lower alkoxycarbonyl, especially ($C_{1-5}$ alkoxy)-carbonyl,
   (7) hydroxy-lower alkyl, especially hydroxy-$C_{1-3}$-alkyl,
   (8) perhalo-lower alkyl, especially perhalo $C_{1-3}$-alkyl, such as trifluoromethyl,
   (9) lower alkoxy, especially $C_{1-3}$ alkoxy, such as methoxy or propoxy,
   (10) cyano,
   (11) perhalo-lower alkylthio, especially perhalo-$C_{1-3}$ alkylthio, such as trifluoromethylthio,
   (12) lower alkylthio, especially $C_{1-3}$ alkylthio, such as methylthio or propylthio,
   (13) lower alkylsulfonyl, especially $C_{1-3}$ alkyl sulfonyl, such as methylsulfonyl or isopropylsulfonyl,
   (14) perhalo-lower alkylsulfonyl, especially perhalo-$C_{1-3}$ alkylsulfonyl, such as trifluoromethylsulfonyl,
   (15) lower alkyl sulfinyl, especially $C_{1-3}$ alkylsulfinyl, such as methylsulfinyl,
   (16) perhalo-alkylsulfinyl, especially perhalo-$C_{1-3}$ alkylsulfinyl, such as trifluoromethylsulfinyl,
   (17) amino,
   (18) lower alkanoylamino, especially $C_{2-6}$ alkanoylamino, such as acetylamino, or pentanoylamino,
   (19) lower alkylamino, especially $C_{1-3}$ alkylamino,
   (20) di(lower alkyl)amino, especially di($C_{1-3}$ alkyl)amino,
   (21) hydroxy,
   (22) N-lower alkylcarbamoyl, especially N-$C_{1-3}$ alkylcarbamoyl,
   (23) N,N-di(lower alkyl)carbamoyl, especially N,N-di($C_{1-3}$ alkyl)carbamoyl,
   (24) nitro,
   (25) di(lower alkyl)sulfamoyl, especially di($C_{1-3}$-alkyl)sulfamoyl,
   (26) lower alkoxycarbonylamino, especially $C_{1-3}$ alkoxycarbonylamino, and
   (27) N-lower alkylcarbamoyloxy, especially $C_{1-3}$ alkylcarbamoyloxy; and
  $R^1$ and $R^2$ are independently selected from hydrogen; lower alkyl, especially $C_{1-3}$ alkyl; lower alkenyl, especially $C_{2-5}$ alkenyl; lower cycloalkyl, especially $C_{3-6}$ cycloalkyl; or $R^1$ and $R^2$ joined together, form with the nitrogen to which they are attached 1-piperidyl, 1-pyrrolidyl, or 4-morpholinyl.

A preferred embodiment of the novel compounds of this invention is the compound of structural formula:

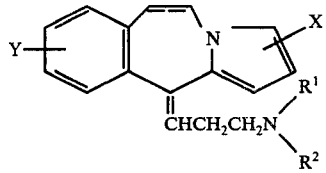

wherein X and Y are as defined above and especially where they are in the 2- and 9- positions, respectively, and $R^1$ and $R^2$ are independently hydrogen or $C_{1-3}$ alkyl.

A still more preferred embodiment of the novel compounds is where one of X and Y is hydrogen, and the other is hydrogen, cyano, formyl, $C_{2-6}$ alkanoyl, or chloro.

Also contemplated within the scope of the present invention are pharmaceutically acceptable N-acid addition salts of the pyrrolobenzazepines of the present invention. Such pharmaceutically acceptable forms, prepared by conventional means, include: the hydrochloride, maleate, sulfate, phosphate, citrate, tartrate, succinate, and the like. These pharmaceutically acceptable salts are generally equivalent in potency to the free amino form taking into consideration the stoichiometric quantities employed.

It will be appreciated that the compounds of the present invention exist as cis-trans or (Z, E) geometrical isomers which are separable by conventional separation techniques such as fractional crystallization and chromatography. Such isomers, individually and mixtures thereof, are within the scope of the present invention.

Unexpectedly, it has been discovered that the above-described pyrrolobenzazepines of the present invention are useful as skeletal muscle relaxants and can be used for treating muscle spasms and other similar muscle disorders associated with or caused by injury, disease, or arising spontaneously with no known cause. Muscle spasm, spasticity and related clinical disorders involving muscle hyperactivity or increased muscle tone affect a large section of the population. Such clinical disorders involving muscle hyperactivity include the spasticity of cerebral origin which may arise from brain injury or tumor. Another related disorder is cerebral palsy. Other clinical disorders involving tonic skeletal muscle hyperactivity are Parkinson's disease, muscular rigidity, and muscle spasm of traumatic origin including low-back and cervical spine syndromes, many orthopedic deformities, arthritic states, myositis, whip-lash injuries, fractures, dislocation, cramps, sciatica, and spinal cord injuries. At present, a variety of medicinals are used in an attempt to relieve or correct the clinical disorders involving muscle hyperactivity including muscle spasm, spasticity, and rigidity and pain associated therewith. But administration of these various materials unfortunately is attended by concomitant side effects and toxicity and/or lack of specificity which limit their usefulness. There is an unsatisfied need at the present time for a medication which has a highly specific effect on the muscle hyperactivity associated with various clinical disorders when administered either by the oral or parenteral route which at the same time has a minimum of side effects or contraindications.

In the method of treatment and pharmaceutical composition aspects of the present invention it is to be noted that the precise unit dosage form and dosage level depend upon the case history of the individual being treated and consequently are left to the discretion of the therapist. In general, however, the compounds of the present invention produce the desired effect of skeletal muscle relaxation when given at from about 0.01 to about 30 mg./kg. body weight per day. Any of the usual pharmaceutical forms may be employed such as tablets, capsules, elexirs, and aqueous suspensions comprising from about 0.01 to about 30.0 mg. of the compounds of this invention per kilogram body weight given daily. Thus for example tablets given 2–4 times per day comprising from about 0.05 to about 75.0 mg. of the compounds of this invention are suitable; however, the preferred range for the unit dosage level in the form of tablets is from about 0.2 to about 40.0 mg. of the compounds of the present invention. Sterile solutions for injection comprising from about 0.1 to 30.0 mg. per dose of the compounds of this invention given 2–4 times daily are also a suitable means of delivery.

The novel compounds of this invention are also tranquilizing agents. For this purpose, they may be administered in the same manner and dosage rates described above for the muscle relaxant utility.

Accordingly, it is an object of the present invention to provide the above-described pyrrolobenzazepines which are useful as skeletal muscle relaxants and tranquilizers. It is a further object of the present invention to provide pharmaceutical compositions comprising such pyrrolobenzazepines and to provide methods of treatment comprising administering such compounds and compositions when a skeletal muscle relaxant and/or tranquilizing effect is indicated.

The novel compounds of this invention are generally prepared in accordance with the following reaction scheme:

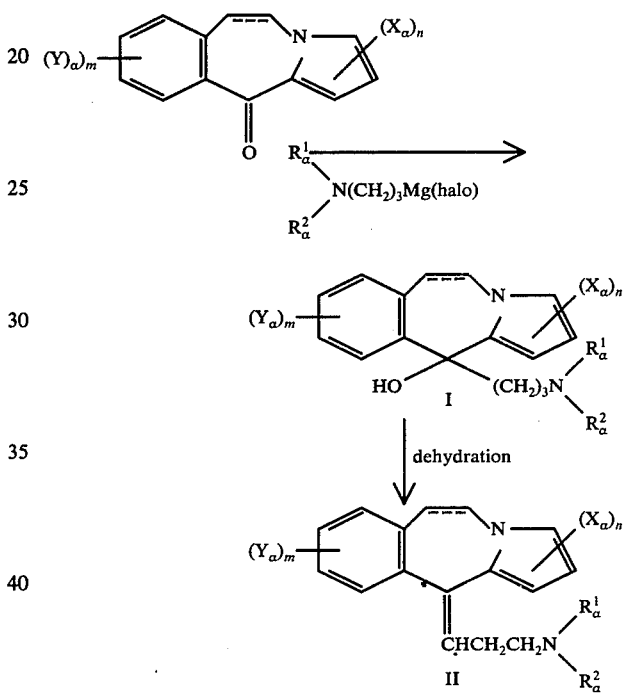

wherein $X_a$ and $Y_a$ are as defined in X and Y but exclusive of formyl; and $R_a^1$ and $R_a^2$ are as defined in $R^1$ and $R^2$ but that they are other than hydrogen. The ketone starting material is treated with a Grignard reagent of formula $R_a^1 R_a^2 N(CH_2)_3 Mg(halo)$ in a solvent such as tetrahydrofuran, ether, or the like at a temperature of from about −10° C. to reflux for from about 10 minutes to about 10 hours to provide the 11-hydroxy-11-alkylated intermediate, which species is then dehydrated by treatment with an acid such as hydrochloric, oxalic, trifluoroacetic, formic, acetic, trifluoroacetic anhydride, trichloroacetic acid, phosphorous oxychloride with a tertiary amine, and the like at a temperature of from about 0° to about 100° C. for from about 5 minutes to about 24 hours to provide the final product pyrrolobenzazepines. The Grignard reaction and the subsequent dehydration described above are substantially identical to those disclosed in U.S. Pat. Nos. 3,014,911 (issued Dec. 26, 1961), 2,951,082 (issued Aug. 30, 1960), 3,428,677 (issued Feb. 18, 1969), 3,428,735 (issued Feb. 18, 1969), 3,454,643 (issued July 8, 1969), and 3,499,037 (issued Mar. 3, 1970), all to Edward L. Engelhardt or Edward L. Engelhardt et al.

Nitro-pyrrolobenzazepines of this invention are also useful as intermediates to the corresponding amino-, alkylamino-, dialkylamino-, and alkanoylamino-pyrrolobenzazepines.

The amino- compounds are prepared by catalytic reduction of the nitro- compounds over a noble metal catalyst, preferably palladium on carbon in a lower alkanol.

The alkylamino- compounds are prepared by heating the corresponding amino compound in a trialkyl orthoformate up to reflux temperature for 2-8 hours, followed by reduction of the product therefrom with an alkali metal borohydride reagent.

The dialkylamino- compounds are prepared by reductive alkylation of the corresponding amine with an aldehyde in the presence of a reducing agent such as sodium cyanoborohydride, hydrogen in the presence of a noble metal catalyst, or refluxing formic acid as in the Eschweiler-Clarke reaction.

The alkanoylamino- compounds are prepared by treatment of the corresponding amine with an alkanoyl anhydride at 20°-50° C. preferably in the presence of an organic base such as pyridine.

Formylpyrrolobenzazepines may be prepared by reduction of the corresponding cyano compound or its carbinol intermediate with nickel-aluminum alloy in formic acid or aqueous formic acid at from 50° C. to reflux temperature for 30 minutes to 5 hours.

Alkyl-, and di(alkyl)carbamoyl compounds may be prepared from the corresponding carboxy compounds by forming the acid chloride therefrom followed by treatment with an alkylamine or a di(alkyl)amine in an inert organic solvent such as methylene chloride or the like, at −20° C. to reflux temperature until the reaction is complete.

Alkoxycarbonyl compounds may be prepared by heating at 50° C. to reflux for 1-8 hours the corresponding carboxy compound in a lower alkanol in the presence of a strong mineral acid, such as hydrogen chloride.

Novel compounds with a trifluoromethylthio or alkylthio substituent in the benzo ring may be prepared by reacting the corresponding iodo- or bromo- compound with trifluoromethylthiocopper (formed by the reaction of copper powder with bis(trifluoromethylthio)mercury) or a cuprous alkylsulfide respectively in a polar organic solvent such as dimethylformamide, quinoline, or hexamethylphosphoramide at 50° to 200° C. for 0.5-24 hours.

Similarly, cyano compounds may be prepared by treating the chloro, bromo- or iodo- compounds with cuprous cyanide.

In the novel compounds of this invention where one of $R^1$ or $R^2$ is hydrogen, they are prepared by reacting a compound wherein one of $R_a^1$ and $R_a^2$ are alkyl with 2,2,2-trichloroethylchloroformate in an organic solvent such as benzene, toluene, or the like at 50°-200° C., conveniently at reflux temperature, for 10-24 hours to provide an intermediate N-2,2,2-trichloroethoxycarbonyl compound. This intermediate is then subjected to reduction, such as with zinc dust in acetic acid at about ambient temperature for 10-24 hours to provide a final product wherein one of $R^1$ or $R^2$ is hydrogen.

Preparation of the secondary amines of this invention is also carried out in a conventional way by reaction of the tertiary amine with cyanogen bromide, as described in R. Adams et al., "Organic Reactions," Vol. VII, pp. 198-262, followed by hydrolysis of the intermediate cyanamide to the desired secondary amine. An alternative well-known route involves heating the tertiary amine with ethyl chloroformate, followed by hydrolysis of the carbamate derivative so formed.

Another procedure for preparing the novel compounds of the present invention is exemplified as outlined below, wherein $X_a$, $Y_a$, $n$, $m$, $R^1$, $R^2$ and the dotted line are as previously defined:

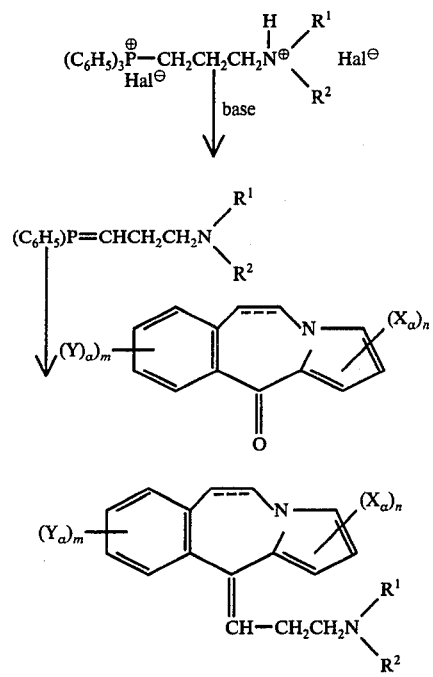

In this procedure, an aminopropylphosphonium halide hydrohalide, prepared as described in U.S. Pat. No. 3,354,155 is converted to an aminopropylidene-trisubstituted phosphorane by treatment with a strong base. This reaction may be carried out in a medium such as dry ether, tetrahydrofuran or dimethylsulfoxide with appropriate strong bases such as alkoxides, alkyl lithium reagents, sodium hydride and the like.

The aminopropylidene-trisubstituted phosphorane so prepared is caused to react with the desired ketone in the solvent in which it is prepared at temperatures from about −10° to about 100° C. for from about 1 to 12 hr., depending on the reactivity of the ketone.

It is to be noted that normally 2 equivalents of strong base are used per equivalent of aminopropylphosphonium halide hydrohalide. However, if the ketone to be used contains one or more "active" hydrogens such as is present in a N—H or O—H functionality, an additional equivalent of strong base is used per "active" hydrogen.

The pure geometric isomers of the present invention can be interconverted by irradiation of a solution of the isomer in question in a solvent such as benzene, acetonitrile, t-butanol, etc. contained in a Dyrex vessel. Such irradiation of a single geometric isomer gives rise to an approximately 1:1 ratio of the two isomers, the extract proportion varying somewhat for each compound. This procedure is useful when one of the geometric isomers is considerably less active than the other, for it permits the conversion of the less active isomer into the more active isomer, which can than be recovered by crystallization of a suitable salt or chromatography of the mixture.

The Grignard reaction product of structural formula:

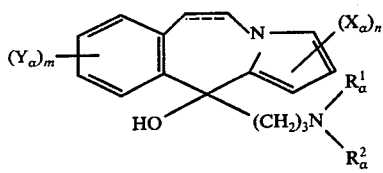

wherein $X_a$, $Y_a$, $n$, $m$, $R_a^1$, $R_a^2$, and the dotted line are as previously defined, forms another embodiment of this invention.

A preferred embodiment of this novel compound is the compound of structural formula:

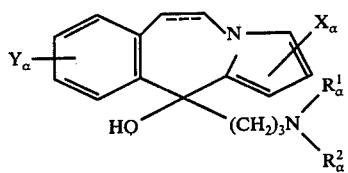

wherein $X_a$ and $Y_a$ are as defined above, and especially where they are in the 2- and 9- positions, respectively, and $R_a^1$ and $R_a^2$ are $C_{1-3}$ alkyl.

A still more preferred aspect is where one of $X_a$ and $Y_a$ is hydrogen and the other is hydrogen, cyano $C_{2-6}$ alkanoyl, or chloro.

The ketones used as starting materials in novel processes of this invention are prepared by the following detailed descriptions.

PREPARATION OF STARTING MATERIALS

GROUP A 6,11-Dihydro-5H-pyrrolo[2,1-b][3]benzazepin-11-ones

Example 1

6,11-Dihydro-5H-pyrrolo[2,1-b][3]benzazepin-11-one

Step A: Preparation of 1-(2-phenethyl)-pyrrole-2-carboxylic acid and 1-(2-phenethyl)-4-cyanopyrrole-2-carboxylic acid Method A: Preparation of 1-(2-phenethyl)pyrrole-2-carboxylic acid Methyl pyrrole-2-carboxylate (10.0 g.) in 100 ml. dimethylformamide (DMF) was treated portionwise with sodium hydride (2.21 g.) at 25° C. After evolution of hydrogen ceased, styrene oxide (11.52 g.) was added and the mixture was heated at 115° C. for 1 hour. The resulting mixture was poured into 600 ml. ice-water and extracted with ether (2 × 100 ml.). The aqueous phase was acidified to pH 1 with 6N HCl to precipitate the product, which was collected by filtration, washed with water and dried, m.p. 183°–185° C.

The unsaturated acid, trans-1-styrylpyrrole-2-carboxylic acid, 24.4 g. was suspended in 200 ml. ethanol in the presence of 1 g. 10% Pd/C and hydrogenated under 3 atmospheres hydrogen until uptake of hydrogen ceased. After removal of the catalyst by filtration, the product, 1-(2-phenethyl)-pyrrole-2-carboxylic acid was obtained by evaporation of solvent, m.p. 124°–125° C.

Method B: Preparation of 1-(2-phenethyl)-4-cyanopyrrole-2-carboxylic acid

To 75 g. of potassium carbonate in 300 ml. of dimethylformamide was added successively 84 g. of 2-phenethyl bromide and 63.5 g. of 2-carbomethoxy-4-cyanopyrrole. The mixture was heated in an oil bath at 85° C. for 4 hours, poured into 1000 ml. of water, and extracted with 3 × 1000 ml. of ether. The combined organic extracts were washed with 2 × 100 ml. of water, dried over magnesium sulfate, filtered and evaporated. The residue was triturated with 500 ml. of fresh ether and the resulting solid was filtered to yield 82.8 gm. (77%) of 1-(2-phenethyl)-2-carbomethoxy-4-cyanopyrrole, m.p. 109°–110° C.

A mixture of 80.3 g. of 1-(2-phenethyl)-2-carbomethoxy-4-cyanopyrrole, 23.3 g. of potassium hydroxide and 900 ml. of ethanol was heated at 75° C. for 2 hours. The solution was evaporated to dryness, the residue was dissolved in 1000 ml. of water, and the solution was acidified to pH 1 with 6N HCl to cause precipitation of 1-(2-phenethyl)-4-cyanopyrrole-2-carboxylic acid. The product was collected by filtration, washed with water and dried to give 72 g. (95%), m.p. 195°–195.5° C.

Following the procedure described in Example 1, Step A, the nuclear substituted 1-(2-phenethyl)-pyrrole-2-carboxylic acids (A) of Table I are obtained when the indicated molar equivalent substitutions for the styrene oxide (B) or 2-(phenethyl) halide (D) and the methyl-pyrrole-2-carboxylate (C) of Example 1 are made:

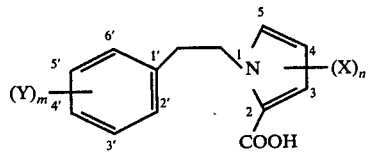

A

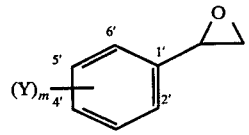 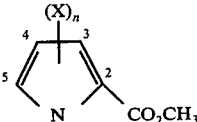

B                C

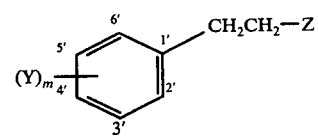

D wherein Z is bromide, iodide, tosylate or mesylate

TABLE I

| Compound | Phenyl Reactant $(Y)_m$ | B or D | Pyrrole Reactant, C $(X)_n$ | Product, A $(Y)_m (X)_n$ | M.P. (° C.) |
|---|---|---|---|---|---|
| 1. | H | (B) | 4-SO$_2$N(CH$_3$)$_2$ | 4-SO$_2$N(CH$_3$)$_2$ | |
| 2. | H | (B) | 4-SO$_2$CH$_3$ | 4-SO$_2$CH$_3$ | |
| 3. | H | (B) | 4-SO$_2$CH(CH$_3$)$_2$ | 4-SO$_2$CH(CH$_3$)$_2$ | |
| 4. | H | (B) | 4-SO$_2$CF$_3$ | 4-SO$_2$CF$_3$ | |
| 5. | H | (D) | 4-CN | 4-CN | 195–195.5 |

TABLE I-continued

| Compound | Phenyl Reactant (Y)$_m$ | B or D | Pyrrole Reactant, C (X)$_n$ | Product, A (Y)$_m$(X)$_n$ | M.P. (° C.) |
|---|---|---|---|---|---|
| 6. | H | (B) | 4-COOC$_2$H$_5$ | 4-COOC$_2$H$_5$ | |
| 7. | H | (D) | 4-NO$_2$ | 4-NO$_2$ | >200 |
| 8. | H | (B) | 4-COCH$_3$ | 4-COCH$_3$ | |
| 9. | H | (B) | 4-CF$_3$ | 4-CF$_3$ | |
| 10. | 4'-O-C(=O)-NHCH$_3$ | (B) | H | 4'-OCONHCH$_3$ | |
| 11. | 4'-NH—COOCH$_3$ | (B) | H | 4'-NHCOOCH$_3$ | |
| 12. | 4'-CH$_3$ | (B) | H | 4'-CH$_3$ | |
| 13. | H | (D) | 4,5-Br$_2$ | 4,5-Br$_2$ | 178–179 |
| 14. | H | (D) | 4-Br | 4-Br | |
| 15. | H | (D) | 4-Cl | 4-Cl | 117–120 |
| 16. | H | (D) | 5-CN | 5-CN | |
| 17. | H | (D) | 3,4,5-Br$_3$ | 3,4,5-Br$_3$ | 182–184 |
| 18. | H | (B) | 4-SCF$_3$ | 4-SCF$_3$ | 123–125 |
| 19. | H | (B) | 4-CON(CH$_3$)$_2$ | 4-CON(CH$_3$)$_2$ | |
| 20. | H | (D) | 4-CH$_3$-3,5-Br$_2$ | 4-CH$_3$-3,5-Br$_2$ | |
| 21. | 4'-NH—COCH$_3$ | (D) | 3,4,5-Br$_3$ | 4'-NHCOCH$_3$-3,4,5-Br$_3$ | |
| 22. | H | (D) | 4-CHO | 4-CHO | |
| 23. | 4'-CH(CH$_3$)$_2$ | (D) | H | 4'-CH(CH$_3$)$_2$ | |
| 24. | 4'-SCH$_3$ | (D) | H | 4'-SCH$_3$ | |
| 25. | 3',4'-(CH$_3$)$_2$ | (D) | 4-CN | 3',4'-(CH$_3$)$_2$-4-CN | |
| 26. | 4'-OH | (D) | 4-CN | 4'-OH-4-CN | |
| 27. | 4'-OCH$_3$ | (D) | 4-CN | 4'-OCH$_3$-4-CN | |
| 28. | 4'-CH$_3$ | (D) | 3,4,5-Br$_3$ | 4'-CH$_3$-3,4,5-Br$_3$ | 170–173 |

Step B: Preparation of 1-(2-phenethyl-2,3-dibromopyrrole-5-carboxylic acid chloride To a solution of 1-(2-phenethyl)pyrrole-2-carboxylic acid (105 g., 0.49 mole) in acetic acid (750 ml.) was added 156 g. of bromine over 30 minutes at 25° C. Formic acid (100 ml.) was added and the reaction chilled in ice, to yield 66 gm. (0.18 moles) of 1-(2-phenethyl)-2,3-dibromopyrrole-5-carboxylic acid after solvent removal. Heating the resulting acid in excess thionyl chloride for 1 hour yielded the acid chloride in near quantitative yield after removal of solvent by evaporation, washing with petroleum ether and drying in vacuum.

Following the procedure of Example 1, Step B, but using chlorine in place of bromine, there is obtained 1-(2-phenethyl)-2,3-dichloro-5-pyrrole carboxylic acid chloride.

Following the procedure of Example 1, Step B, the mono- and dibrominated acid chlorides depicted in Table II are obtained when an equivalent amount of the appropriate free acid from Table I replaces the 1-(2-phenethyl)-pyrrole-2-carboxylic acid used in Example 1, Step B, and either 1 or 2 equivalents of bromine is reacted therewith.

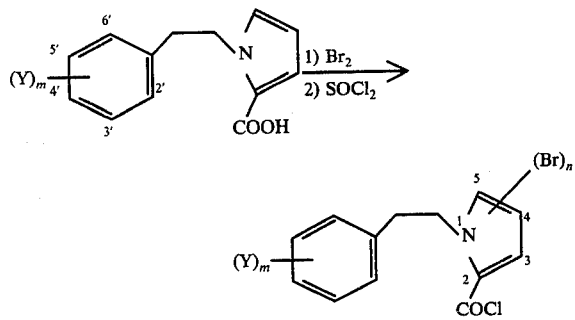

TABLE II

| Starting material from | (Y)$_m$ | Equivalents of Bromine | (Br)$_n$ |
|---|---|---|---|
| Example 1A | H | 1 | 4-Br |
| Table I(12) | 4'-CH$_3$ | 2 | 4,5-Br$_2$ |
| Table I(10) | 4'-OCONHCH$_3$ | 2 | 4,5-Br$_2$ |
| Table I(11) | 4'-NHCOOCH$_3$ | 2 | 4,5-Br$_2$ |

TABLE II-continued

| Starting material from | (Y)$_m$ | Equivalents of Bromine | (Br)$_n$ |
|---|---|---|---|
| Table I(24) | 4'-SCH$_3$ | 2 | 4,5-Br$_2$ |
| Table I(23) | 4'-CH(CH$_3$)$_2$ | 2 | 4,5-Br$_2$ |

Following the procedure of Example 1, Step B, but omitting the nuclear halogenation step, there is obtained the corresponding acid chlorides when the 1-(2-phenethyl)-pyrrole-2-carboxylic acid of Example 1, Step B, is replaced by an equivalent amount of the free acids enumerated in Table I, respectively.

Step C: Preparation of 2,3-dibromo-6,11-dihydro-5H-pyrrolo[2,1-b][3]benzazepin-11-one To a solution of 1-(2-phenethyl)-4,5-dibromopyrrole-2-carboxylic acid chloride (40 g., 0.102 mole) in 800 ml. sym-tetrachloroethane at 140° C. was added 40 gm. (0.30 mole) of aluminum chloride. After three minutes, the reaction was cooled in ice, poured over 2000 g. of ice, stirred for 10 minutes, filtered, and the organic layer was separated. The aqueous layer was extracted with 2 × 200 ml. of chloroform, which was combined with the first organic layer. The combined organic solution was washed with 3 × 500 ml. of water, dried and evaporated in vacuum to provide a dark oil (29 g.) which was chromatographed on silica gel using benzene to elute in 50 ml. fractions. Fractions 5–13 were combined and evaporated to yield 20.3 gm. (0.057 moles) of 2,3-dibromo-6,11-dihydro-5H-pyrrolo[2,1-b][3]benzazepin-11-one, m.p. 130°–132° C.

Following the procedure of Example 1, Step C, but substituting for the 1-(2-phenethyl)-4,5-dibromopyrrole-2-carboxylic acid chloride used therein an equimolecular amount of the acid chlorides prepared in accordance with Example 1, Step B, there are produced the 6,11-dihydro-5H-pyrrolo[2,1-b][3]benzazepin-11-ones described in Table III by the following process:

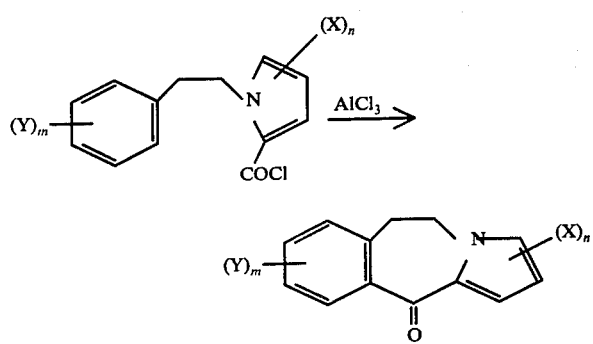

Table III

| Compound[a] | (Y)$_m$ | (X)$_n$ | m.p. (° C.) |
|---|---|---|---|
| 1 | H | 2-SO$_2$N(CH$_3$)$_2$ | |
| 2 | H | 2-SO$_3$CH$_3$ | |
| 3 | H | 2-SO$_2$CH(CH$_3$)$_2$ | |
| 4 | H | 2-SO$_2$CF$_3$ | |
| 5 | H | 2-CN | 146–147 |
| 6 | H | 2-CO$_2$C$_2$H$_5$ | |
| 7 | H | 2-NO$_2$ | 174–176 |
| 8 | H | 2-COCH$_3$ | 160–161* |
| 9 | H | 2-CF$_3$ | |
| 10 (II 3) | 9-OCONHCH$_3$ | 2,3-Br$_2$ | |
| 11 (II 4) | 9-NHCOOCH$_3$ | 2,3-Br$_2$ | |
| 12 (II 2) | 9-CH$_3$ | 2,3-Br$_2$ | |
| 13 | H | 2,3-Br$_2$ | 130–132 |
| 14 (II 1) | H | 2-Br | 101–103 |
| 15 | H | 2-Cl | 100–105 |
| 16 | H | 3-CN | 130–131* |
| 17 | H | 1,2,3-Br$_3$ | 150–155 |
| 18 | H | 2-SCF$_3$ | 77–78* |
| 19 | H | 2-CON(CH$_3$)$_2$ | 148–149.5* |
| 20 | H | 1,3-Br$_2$-2-CH$_3$ | |
| 21 | 9-NHCOCH$_3$ | 1,2,3-Br$_2$ | |
| 22 | H | 2-CHO | 135–136* |
| 23 (II 6) | 9-CH(CH$_3$)$_2$ | 2,3-Br$_2$ | |
| 24 (II 5) | 9-SCH$_3$ | 2,3-Br$_2$ | |
| 25 | 8,9-(CH$_3$)$_2$ | 2-CN | |
| 26 | 9-OH | 2-CN | |
| 27 | 9-OCH$_3$ | 2-CN | |
| 28 | 9-CH$_3$ | 1,2,3-Br$_3$ | 160–163 |
| 29(Ex. 1, Step B) | H | 2,3-Cl$_2$ | |

[a] The numbers of the compounds described in Table III correspond to the numbers of the starting materials described in Table I from which they were prepared, unless otherwise indicated. For example, compound 5 of Table III was prepared from the compound 5 of Table 1. Compound 12 was prepared from compound 2 of Table II.
*m.p. of material made by different route.

Step D: Preparation of 6,11-dihydro-5H-pyrrolo[2,1-b][3]benzazepin-11-one

A suspension of 25 g. (0.070 mole) of 2,3-dibromo-6,11-dihydro-5H-pyrrolo[2,1-b][3]benzazepin-11-one in 200 ml. ethanol containing 25 ml. of triethylamine and 1 gm. of 10% Pd on charcoal was hydrogenated under 3 atmospheres of hydrogen to yield 6,11-dihydro-5H-pyrrolo[2,1-b][3]benzazepin-11-one, m.p. 54°–55° C. after removal of catalyst, recrystallization from petroleum ether and drying under vacuum. The same compound is also obtained by hydrogenolysis of the 2,3-dichloro ketone and the 1,2,3-tribromoketone.

Following the procedure of Example 1, Step D, but substituting for the 2,3-dibromo-6,11-dihydro-5H-pyrrolo[2,1-b][3]benzazepin-11-ones used therein, an equimolecular amount of the halogenated ketones described in Table III, there are produced the ketones described in Table IV.

Table IV

| Starting Material | | | |
|---|---|---|---|
| Table | Compound No. | (Y)$_m$ | (X)$_n$ |
| III | 10 | 9-OCONHCH$_3$ | H |
| III | 11 | 9-NH—COOCH$_3$ | H |
| III | 12 | 9-CH$_3$ | H |
| III | 14 | H | H |
| III | 23 | 9-CH(CH$_3$)$_2$ | H |
| III | 20 | H | 2-CH$_3$ |
| III | 21 | 9-NH—COCH$_3$ | H |
| III | 24 | 9-SCH$_3$ | H |
| III | 28 | 9-CH$_3$ | H (oil) |

Example 2

Preparation of 2-cyano-6,11-dihydro-5H-pyrrolo[2,1-b][3]benzazepine-11-one

To a solution of 73.6 g. of 1-(2-phenethyl)-4-cyanopyrrole-2-carboxylic acid chloride in 850 ml. of tetrachloroethane maintained at 140° C. is added over a period of 2 minutes 114 g. of aluminum chloride. The resulting solution is stirred at 140° C. for 4 minutes, poured over 2000 g. of ice and the mixture stirred for 10 minutes. It is then filtered to remove insoluble tarry material and the organic layer separated. The aqueous layer is extracted with 2 × 500 ml. of chloroform, which is combined with the original organic layer, washed with 500 ml. of water and with 200 ml. portions of 1N sodium bicarbonate until the aqueous washes remain basic. The organic layer is dried over magnesium sulfate, filtered and evaporated under vacuum to leave a residue. This residue upon trituration with 300 ml. of ether readily crystallizes. The crystals are filtered and air-dried to yield 57.2 gm. (90%) of 2-cyano-6,11-dihydro-5H-pyrrolo[2,1-b][3]benzazepin-11-one, m.p. 146°–147° C.

Example 3

Preparation of 2-formyl-6,11-dihydro-5H-pyrrolo[2,1-b][3]benzazepine-11-one

2-Cyano-6,11-dihydro-5H-pyrrolo[2,1-b][3]benzazepin-11-one (222 mg.) and 222 mg. nickel-aluminum alloy in 2 ml. 75% formic acid is refluxed for 1½ hours. The solid is filtered off and washed with ethanol. The filtrate is diluted with 50 ml. water and extracted twice with 50 ml. methylene chloride. The organic layer is washed with water, 5% sodium bicarbonate and with water; it is then dried over magnesium sulfate and evaporated to dryness. Addition of ether induces crystallization and the crystals are filtered and air-dried to yield 125 mg. (56%) 2-formyl-6,11-dihydro-5H-pyrrolo[2,1-b][3]benzazepine-11-one, m.p. 135°–136° C.

Example 4

2-Carbamoyl-6,11-dihydro-5H-pyrrolo[2,1-b][3]benzazepin-11-one

2-Cyano-6,11-dihydro-5H-pyrrolo[2,1-b][3]benzazepin-11-one (30 g., 0.135 mole) in 100 ml. of concentrated hydrochloric acid and 100 ml. of acetic acid was refluxed for 2 hours. It was then poured onto 500 ml. of water and continuously extracted with methylene chloride. The solution, from which crystals deposited during the extraction, was left to cool to room temperature and filtered to afford 2-carbamoyl-6,11-dihydro-11-oxo-5H-pyrrolo[2,1-b][3]benzazepine (27 g. 83%), m.p. 228° C.

Example 5

6,11-Dihydro-11-oxo-5H-pyrrolo[2,1-b][3]benzazepine-2-carboxylic acid

To 2-carbamoyl-6,11-dihydro-pyrrolo[2,1-b][3]benzazepine-11-one (27 g., 0.112 moles) in 300 ml. of 50% sulfuric acid maintained over 50° C., was added slowly 25 g. of sodium nitrite in 75 ml. of water. At the end of the addition, the solid was filtered, washed with water and air-dried to yield 6,11-dihydro-11-oxo-pyrrolo[2,1-b][3]benzazepine-2-carboxylic acid (24 g., 89%), m.p. 287°–290° C.

Example 6

2-Dimethylcarbamoyl-6,11-dihydro-5H-pyrrolo[2,1-b][3]benzazepin-11-one
Step A: Preparation of 2-chlorocarbonyl-6,11-dihydro-5H-pyrrolo[2,1-b][3]benzazepin-11-one 6,11-Dihydro-11-oxo-pyrrolo[2,1-b][3]benzazepine-2-carboxylic acid (24 g., 99 mmoles) in 100 ml. of thionyl chloride was refluxed for 15 minutes. The volatiles were removed under vacuum and the residue was triturated in ether. Filtration and air-drying yielded 2-chlorocarbonyl-6,11-dihydro-5H-pyrrolo[2,1-b][3]benzazepin-11-one (23 g., 89%), m.p. 147°–148.5°.

Step B: Preparation of 2-dimethylcarbamoyl-6,11-dihydro-5H-pyrrolo[2,1-b][3]benzazepine-11-one Anhydrous dimethylamine was bubbled through a suspension of 2-chlorocarbonyl-6,11-dihydro-5H-pyrrolo[2,1-b][3]benzazepin-11-one (23 g., 88.5 mmoles) in 100 ml. of methylene chloride. (Note: the introduction of dimethylamine caused the mixture to reflux and this reflux stopped when all the acid chloride was reacted. This took about 1 hour and complete solution was obtained.)

The reaction mixture was washed with water and dried over sodium sulfate. It was then taken to dryness, triturated in ether, filtered and air-dried to yield 2-dimethylcarbamoyl-6,11-dihydro-5H-pyrrolo[2,1-b][3]benzazepin-11-one (20 g., 84%), m.p. 148°–149.5° C.

Example 7

6,11-Dihydro-2-methoxycarbonyl-5H-pyrrolo[2,1-b][3]benzazepin-11-one 6,11-Dihydro-11-oxo-5H-pyrrolo[2,1-b][3]benzazepine-2-carboxylic acid (25.5 g., 0.11 moles) in 300 ml. of methanol saturated with hydrogen chloride was refluxed until a homogeneous solution was obtained (4 hours).

The volatiles were removed under vacuum and the residue was dissolved in 300 ml. of methylene chloride, washed with dilute sodium hydroxide and then with water. It was dried over sodium sulfate and concentrated. The residue was triturated in ether, filtered and air-dried, yielding 6,11-dihydro-2-methoxycarbonyl-5H-pyrrolo[2,1-b][3]benzazepin-11-one (23.5 g., 85%), m.p. 125°–127° C.

Example 8

2-Trifluoromethylthio- and 3-trifluoromethylthio-6,11-dihydro-5H-pyrrolo[2,1-b][3]benzazepin-11-one 6,11-Dihydro-5H-pyrrolo[2,1-b][3]benzazepine-11-one (9.6 g., 48.7 mmoles) dissolved in pyridine (20 ml.) and chloroform (50 ml.) was treated with trifluoromethylsulfenyl chloride (12 g., 86.6 mmoles) in chloroform (50 ml.). The reaction mixture was left at room temperature for 2 hours.

The mixture was washed with water, dried over sodium sulfate and concentrated to 16.2 g. of a black oil.

This oil was adsorbed on 800 g. of silica gel. Elution with petroleum ether-ether 3:1 (v/v) yielded 3-trifluoromethylthio-6,11-dihydro-5H-pyrrolo[2,1-b][3]benzazepine-11-one (8.4 g., 57.7%), m.p. 95°–95.5° C.

Elution with ether yielded 2-trifluoromethylthio-6,11-dihydro-5H-pyrrolo[2,1-b][3]benzazepine-11-one (4.2 g., 28.8%), m.p. 77°–78° C.

Example 9

6,11-Dihydro-1-trifluoromethyl-(and -3-trifluoromethyl)-5H-pyrrolo[2,1-b][3]benzazepin-11-one A mixture of 8.9 g. of 6,11-dihydro-5H-pyrrolo[2,1-b][3]benzazepin-11-one, 30 of trifluoromethyl iodide, 20 ml. of pyridine and 300 ml. of acetonitrile was irradiated with a 450 watt lamp for 18 hours. The mixture was evaporated to dryness, and the residue was extracted with ether and filtered. The filtrate was evaporated to an oil. The oil was again treated with 25 g. of trifluoromethyl iodide in pyridine/acetonitrile and irradiated for 12 hours. Evaporation to dryness, extraction with ether, filtration and evaporation to dryness gave a crystalline residue. The residue was chromatographed on silica gel, by elution with benzene. Fraction 1 from the column provided 3.5 g. of product contaminated with traces of the 2-trifluoromethyl isomer. Fraction 2 provided 900 mg. of pure 6,11-dihydro-3-trifluoromethyl-5H-pyrrolo[2,1-b][3]benzazepin-11-one, m.p. 90°–93° C.

Rechromatography of Fractions 3–5 provided pure 6,11-dihydro-1-trifluoromethyl-5H-pyrrolo[2,1-b][3]benzazepin-11-one, m.p. 102°–103° C.

Example 10

6,11-Dihydro-2-pentanoyl-5H-pyrrolo[2,1-b][3]benzazepin-11-one 6,11-Dihydro-5H-pyrrolo[2,1-b][3]benzazepin-11-one (1.0 g.) was dissolved in 20 ml. of methylene chloride and 2.66 g. of aluminum chloride was added with cooling. At room temperature there was added little by little 720 mg. of pentanoyl chloride. Fifteen minutes after the addition was complete the mixture was poured onto ice. The organic phase was separated, filtered, dried and concentrated to dryness. The residue was triturated with ether, collected and dried to give 1.18 g. (85%) of 6,11-dihydro-2-pentanoyl-5H-pyrrolo[2,1-b][3]benzazepin-11-one, m.p. 135°–136° C. Chromatography on silica gel by elution with benzene, and 5% (v/v) ethylacetate in benzene, raised the melting point to 137°–138° C.

Employing the procedure substantially as described in Example 10, but substituting for the pentanoyl chloride used therein, the acid chlorides described in Table V, there are produced the acyl-pyrrolobenzazepinones also described in Table V by the following procedure:

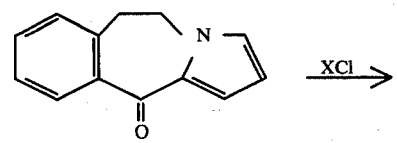

-continued

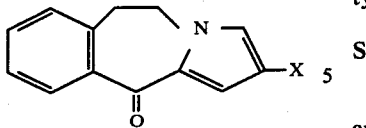

TABLE V

| X | product m.p. (° C.) |
|---|---|
| —C(O)—CH₃ | 160–161 |
| —C(O)—CH(CH₃)₂ | 124–126 |
| —SO₂N(CH₃)₂ [a] | 134–137 |

[a] reaction conducted in nitromethane at reflux temperature for 20 minutes.

Following the procedure of Example 10, but conducting the reaction at 100°–130° C. with excess alkanoyl chloride as solvent and without the aluminum chloride, there are produced mixtures of 2- and 3- alkanoyl ketones which upon chromatographic separation on silica gel provide the alkanoyl ketone products described in Table V and in Example 10 as well as the corresponding 3-pentanoyl-, 3-acetyl-, and 3-isobutyroyl- compounds.

Example 11

9-Iodo-6,11-dihydro-5H-pyrrolo[2,1-b][3]benzazepin-11-one

Step A: Preparation of 7-nitro-3,4-dihydro-isocarbostyril

Fuming nitric acid (17 ml.) was added to 670 ml. of concentrated sulfuric acid at 0° C. 3,4-Dihydro-isocarbostyril (50 g.) was added portionwise maintaining the temperature below 0° C. After 30 minutes at 0° C., the solution was poured into 8 l. of ice water. The crystalline precipitate is collected, washed with water and air dried to give 62.0 g. (95%) of 7-nitro-3,4-dihydro-isocarbostyril, m.p. 225°–230° C. After recrystallization from acetone it has m.p. 230°–232° C.

Step B: Preparation of 7-amino-3,4-dihydro-isocarbostyril

The product from Step A (20 g.) was hydrogenated over 2.0 g. of 10% Pd/C in 350 ml. of methanol. The mixture was filtered, and the filtrate was evaporated to dryness. The residue was suspended in ether and collected on a filter to give 15.7 g. (93%) of 7-amino-3,4-dihydro-isocarbostyril, m.p. 123°–125° C.

Step C: Preparation of 7-iodo-3,4-dihydro-isocarbostyril

A solution of 690 mg. of sodium nitrite in 5 ml. of water was added dropwise to an ice-cold solution of 1.62 g. of 7-amino-3,4-dihydro-isocarbostyril in 4 ml. of concentrated hydrochloric acid and 12 ml. of water. After about 15 minutes at 0°–5° C. a solution of 1.7 g. of potassium iodide in 1 ml. of water was added and the mixture was allowed to warm to room temperature. Acetone (20 ml.) was added and the solution was held at room temperature for 1 hour and at 50°–60° C. for 1 hour. The mixture was concentrated to dryness. The residue was taken up in water, extracted with chloroform, the extract was dried and concentrated to dryness to give 2.0 g. (73%) of 7-iodo-3,4-dihydro-isocarbostyril.

Step D: Preparation of 2-aminoethyl-5-iodobenzoic acid hydrochloride

A mixture of 1.0 g. of 7-iodo compound from Step C and 40 ml. of concentrated hydrochloric acid was heated in a pressure vessel at 145° C. for 30 hours. The solution was concentrated to dryness. The residue was suspended in ether and collected to give 950 mg. (80%) of 2-aminoethyl-5-iodobenzoic acid hydrochloride, m.p. 200°–205° C.

Step E: Preparation of 2-(2-pyrrol-1-yl)ethyl-5-iodobenzoic acid

A mixture of 12.1 g. of product from Step D, 6.48 g. of 2,5-dimethoxytetrahydrofuran, 180 ml. of water and 30 ml. of acetic acid was stirred at 55° C. for 2 hours and at room temperature overnight. The mixture was diluted with water, extracted with chloroform, and the extract was extracted with 0.5% (w/v) sodium hydroxide solution. The alkaline extract was acidified with 6N hydrochloric acid and extracted with chloroform. The extract was dried, filtered and concentrated to dryness. The oily residue was triturated with cyclohexane and the solids were collected to give 8.1 g. (58%) of 2-(2-pyrrol-1-yl)ethyl-5-iodobenzoic acid, m.p. 92°–95° C.

Step F: Preparation of 9-iodo-6,11-dihydro-5H-pyrrolo[2,1-b][3]benzazepin-11-one A mixture of 1 g. of the product from Step E and 20 ml. of polyphosphate ester was stirred 1.5 hrs. at room temperature. The mixture was cooled in ice and diluted with 75 ml. of water. The mixture was extracted with benzene and the extract was washed with water, dried and concentrated to dryness to give 500 mg. of 9-iodo-6,11-dihydro-5H-pyrrolo[2,1-b][3]benzazepin-11-one, which after recrystallization from cyclohexane had m.p. 120°–122° C.

Following the procedure of Example 11, Steps C, D, E, and F. but substituting for the potassium iodide used in Step C thereof an equimolecular amount of cuprous chloride, there is prepared 9-chloro-6,11-dihydro-5H-pyrrolo[2,1-b][3]benzazepin-11-one, m.p. 93°–94° C.

Similarly, by substituting cuprous bromide for the potassium iodide used in Step C of Example 11 or by carrying out the diazotization in 50% aqueous fluoroboric acid instead of hydrochloric acid, there are obtained 9-bromo-6,11-dihydro-5H-pyrrolo[2,1-b][3]benzazepin-11-one and 9-fluoro-6,11-dihydro-5H-pyrrolo[2,1-b][3]benzazepin-11-one, respectively.

Example 12

9-Trifluoromethylthio-6,11-dihydro-5H-pyrrolo[2,1-b][3]benzazepin-11-one

A mixture of 2.4 g. of iodoketone (from Example 11), 5.14 g. of copper (electrolytic dust), 9.0 g. of bis(trifluoromethylthio)mercury and 20 ml. of dimethyl formamide was stirred and heated on a steam bath for 5 hours. The mixture was cooled in ice, treated with 75 ml. of benzene and treated dropwise with 50 ml. of 10% sodium hydroxide solution. After 1 hour at room temperature the mixture was filtered through diatomaceous earth followed by a benzene wash. The filtrate was extracted with benzene. The combined benzene fractions were washed with water, dried, filtered and concentrated to dryness to give 2.0 g. (90%) of 9-trifluoromethylthio-6,11-dihydro-5H-pyrrolo[2,1-b][3]benzazepin-11-one, m.p. 81°–83° C.

Following the procedure of Example 12, but substituting for the copper dust and the bis(trifluoromethylthio)mercury used therein an equimolecular amount of cuprous methylsulfide or cuprous isopropylsulfide, there are produced 9-methylthio-6,11-dihydro-5H-pyrrolo[2,1-b][3]benzazepin-11-one, respectively.

Example 13

9-Nitro-6,11-dihydro-5H-pyrrolo[2,1-b][3]benzazepin-11-one

Following the procedure of Example 11, Steps D, E, and F, but substituting for the 7-iodo-3,4-dihydroisocarbostyril used in Step D thereof, an equimolecular amount of 7-nitro-3,4-dihydro-isocarbostyril, there is produced in sequence:

Step A: 2-aminomethyl-5-nitrobenzoic acid, m.p. 230°–232° C.;
Step B: 2-(2-pyrrol-1-yl)ethyl-5-nitrobenzoic acid, m.p. 147°–149° C.;
Step C: 9-nitro-6,11-dihydro-5H-pyrrolo[2,1-b][3]benzazepin-11-one, m.p. 190°–192° C.

Example 14

9-Amino-6,11-Dihydro-5H-pyrrolo[2,1-b][3]benzazepin-11-one

Following the procedure of Example 11, Step B, but substituting for the 7-nitro-3,4-dihydro-isocarbostyril used therein an equimolecular amount of 9-nitro-6,11-dihydro-5H-pyrrolo[2,1-b][3]benzazepin-11-one, there is produced 9-amino-6,11-dihydro-5H-pyrrolo[2,1-b][3]benzazepin-11-one, m.p. 166°–167° C.

Example 15

9-Methylamino-6,11-dihydro-5H-pyrrolo[2,1-b][3]benzazepin-11-one

A solution of 9-amino-6,11-dihydro-5H-pyrrolo[2,1-b][3]benzazepin-11-one in triethyl orthoformate (2.14 g.; 10 mmoles in 80 ml) is refluxed for 5 hours. The volatiles are removed under vacuum and the residue dissolved in 100 ml. of absolute ethanol is stirred in an ice bath as sodium borohydride (0.88 g.; 0.024 moles) is added over a period of 10 minutes. The mixture is stirred for a period of 2 hours. After concentration of the ethanol, the residue is dissolved in ethyl acetate, washed with water, dried over $Na_2SO_4$ and concentrated to dryness to yield 9-methylamino-6,11-dihydro-5H-pyrrolo[2,1-b][3]benzazepin-11-one.

Example 16

9-Dimethylamino-6,11-dihydro-5H-pyrrolo[2,1-b][3]benzazepin-11-one

To a solution of 9-amino-6,11-dihydro-5H-pyrrolo[2,1-b][3]benzazepin-11-one (2.1 g., 10 mmoles) and 4 ml. (50 mmoles) of 37% aqueous formaldehyde in 15 ml. of acetonitrile is added 1 g. (16 mmoles) of sodium cyano borohydride. A vigorous and exothermic reaction takes place and a dark residue separates. The mixture is stirred for 15 minutes and then glacial acetic acid is added dropwise until the solution tests neutral on wet pH paper. Stirring is maintained for an additional 2 hours. The volatiles are removed under vacuum, and the residue is dissolved in chloroform. The solution is washed with base and with water, dried over sodium sulfate, and concentrated to leave a residue that is purified by chromatography on silica gel. Elution with chloroform yields 9-dimethylamino-6,11-dihydro-5H-pyrrolo[2,1-b][3]benzazepin-11-one as a dark brown oil.

Example 17

9-Cyano-6,11-dihydro-5H-pyrrolo[2,1-b][3]benzazepin-11-one

A stirred mixture of 1 gm. of 9-iodo-6,11-dihydro-5H-pyrrolo[2,1-b][3]benzazepin-11-one, 1 gm. of cuprous cyanide and 5 ml. of dimethylformamide is heated to reflux for 5 hr. The mixture is then poured into a solution of 4 gm. of ferric chloride hydrate in 25 ml. of 2N hydrochloric acid. After stirring the resulting mixture at 60° for 30 min., it is extracted with 3 × 50 ml. of ethyl acetate, the organic extracts washed with 3 × 100 ml. of water and dried over $Na_2SO_4$. Evaporation of the dried solution yields 9-cyano-6,11-dihydro-5H-pyrrolo[2,1-b][3]benzazepin-11-one, m.p. 127°–128° C.

Example 18

9-Trifluoromethylsulfinyl-6,11-dihydro-5H-pyrrolo[2,1-b][3]benzazepin-11-one

A solution of 3 gm. of 9-trifluoromethylthio-6,11-dihydro-5H-pyrrolo[2,1-b][3]benzazepin-11-one in 25 ml. of acetic acid containing 3 ml. of 50% hydrogen peroxide is stirred at 25° C. for 6 hr. The solvent is evaporated and the residue dissolved in 100 ml. of methylene chloride. The solution is washed with 2 × 25 ml. of 5% $Na_2CO_3$ solution, dried and evaporated. Chromatography of the residue on silica gel yields 9-trifluoromethylsulfinyl-6,11-dihydro-5H-pyrrolo[2,1-b][3]benzazepin-11-one.

Employing the procedure of Example 18, but substituting for the 9-trifluoromethylthio-6,11-dihydro-5H-benzazepin-11-one used therein, an equimolecular amount of the corresponding 9-methylthio- or 9-isopropylthio- compounds, there are produced respectively 9-methylsulfinyl-6,11-dihydro-5H-pyrrolo[2,1-b][3]benzazepin-11-one and 9-isopropylsulfinyl-6,11-dihydro-5H-pyrrolo[2,1-b][3]benzazepin-11-one.

Example 19

9-Trifluoromethylsulfonyl-6,11-dihydro-5H-pyrrolo[2,1-b][3]benzazepin-11-one

A solution of 2 gm. of 9-trifluoromethylsulfinyl-6,11-dihydro-5H-pyrrolo[2,1-b][3]benzazepin-11-one in 20 ml. of acetic acid containing 5 ml. of 90% hydrogen peroxide is stirred at 25° C. for 4 days. The solvent is evaporated and the residue dissolved in 100 ml. of methylene chloride. After washing the organic solution with 2 × 25 ml. of 1N $Na_2CO_3$, it is dried and evaporated, and the residue chromatographed on silica gel to yield 9-trifluoromethylsulfonyl-6,11-dihydro-5H-pyrrolo[2,1-b][3]benzazepin-11-one.

Employing the procedure of Example 18, but substituting for the 9-trifluoromethylthio-6,11-dihydro-5H-pyrrolo[2,1-b][3]benzazepin-11-one used therein, an equimolecular amount of the corresponding 9-methylthio- or 9-isopropylthio- compounds, there are produced respectively 9-methylsulfonyl-6,11-dihydro-5H-pyrrolo[2,1-b][3]benzazepin-11-one and 9-isopropylsulfonyl-6,11-dihydro-5H-pyrrolo[2,1-b][3]benzazepin-11-one.

Example 20

9-Formyl-6,11-dihydro-5H-pyrrolo[2,1-b][3]benzazepin-11-one

Employing the procedure of Example 3 but substituting for the 2-cyano compound used therein, an equimolecular amount of 9-cyano-6,11-dihydro-5H-pyrrolo[2,1-b][3]benzazepine there is produced 9-formyl-6,11-dihydro-5H-pyrrolo[2,1-b][3]benzazepin-11-one.

Example 21

9-Trifluoromethyl-6,11-dihydro-5H-pyrrolo[2,1-b][3]benzazepin-11-one

A mixture of 5 g. of the 9-iodo ketone, 25 g. of trifluoromethyl iodide, 9 g. of precipitated copper and 150 ml. of dimethylformamide is heated in a stainless steel tube with shaking for 12 hr. at 140° C. Work-up of the reaction mixture and chromatography yield the title compound.

PREPARATION OF STARTING MATERIAL

GROUP B

11H-Pyrrolo[2,1-b][3]Benzazepines

Example 1

2-Cyano-11H-pyrrolo[2,1-b][3]benzazepin-11-one

Step A: Preparation of trans-2-carboxy-4-cyano-N-styrylpyrrole

A mixture of 5 g. of sodium hydride and 15 g. of methyl 4-cyanopyrrole-2-carboxylate, in 75 ml. of dimethyl formamide was stirred until evolution of hydrogen ceased. Styrene oxide (16 g.) was added and heated at 110° C. for 6 hours. The mixture was poured into 300 ml. of water and extracted with 2 × 150 ml. of ether. The aqueous phase was purged with nitrogen and acidified with 2 N hydrochloric acid. The precipitated solid is collected, washed with water, air dried and washed with ether to give 6.4 g. of pure trans-2-carboxy-4-cyano-N-styrylpyrrole, m.p. 195°–196° C. (decarboxylation).

The sodium hydride used in the above step can be replaced by an equimolecular amount of potassium t-butoxide.

Step B: Preparation of cis-2-carboxy-4-cyano-N-styrylpyrrole

A solution of 50 mg. of trans-2-carboxy-4-cyano-N-styrylpyrrole in 1 ml. of acetonitrile was irradiated with a 450 watt lamp for 45 minutes. The solution was concentrated to dryness. The residue was triturated with ether and the product was collected and air dried to give 37 mg. of cis-2-carboxy-4-cyano-N-styrylpyrrole, m.p. 166°–168° C.

Following the procedure substantially as described in Example 1, Steps A and B, but substituting for the methyl 4-cyanopyrrole-2-carboxylate and styrene oxide used in Step A thereof, equimolecular amounts of the methyl pyrrole carboxylates and styrene oxides, respectively, depicted in Table I, there are produced the cis-N-styryl-pyrrole-2-carboxylic acids, also depicted in Table I by the following process.

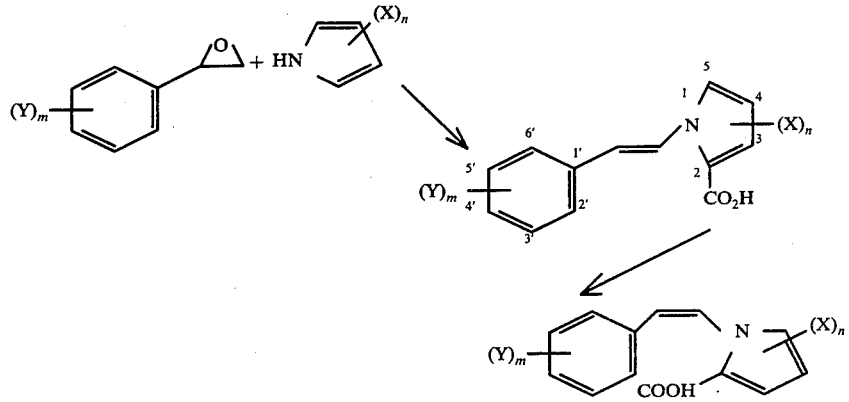

Table I

| Compound | $(Y)_m$ | $(X)_n$ |
|---|---|---|
| 1 | H | H |
| 2 | H | 4-SCF$_3$ |
| 3 | 4'-Cl | H (m.p. 178–180° C.) |
| 4 | 4'-SCF$_3$ | H |
| 5 | 4'-CN | H |
| 6 | H | 4-COCH(CH$_3$)$_2$ |
| 7 | H | 4-SO$_2$N(CH$_3$)$_2$ |
| 8 | H | 4-SO$_2$CH(CH$_3$)$_2$ |
| 9 | H | 4-Cl |
| 10 | 4'-Br | H (m.p. 166–172° C.) |
| 11 | H | 4-NO$_2$ |
| 12 | 4'-OCH$_3$ | H |
| 13 | 4'-CF$_3$ | H |
| 14 | 4'-Cl | 4-CN (m.p. 193–196° C.) |
| 15 | 4'-I | H |
| 16 | 4'-F | H |

Step C: Preparation of 2-cyano-11H-pyrrolo[2,1-b][3]benzazepin-11-one

A solution of 35 mg. cis-2-carboxy-4-cyano-N-styrylpyrrole in 0.5 ml. of dry methylene chloride was treated with 45 µl. of trifluoroacetic anhydride and stirred for 5 minutes. Stannic chloride (45 µl.) was added and the mixture stirred for 15 minutes. The mixture was poured into water, neutralized with ammonium hydroxide and extracted twice with chloroform. The extract was washed with water, dried over sodium sulfate, and concentrated to dryness. Trituration of the residue with 0.5 ml. of ethyl acetate and filtering gave 2-cyano-11H-pyrrolo[2,1-b][3]-benzazepin-11-one, m.p. 197° C.

Following the procedure substantially as described in Example 1, Step C, but substituting for the cis-2-carboxy-4-cyano-N-styrylpyrrole used therein, an equimolecular amount of the cis-styrylpyrroles from Table I, there are produced the 11H-pyrrolo[2,1-b][3]benzazepine-11-ones described in Table II, by the following process:

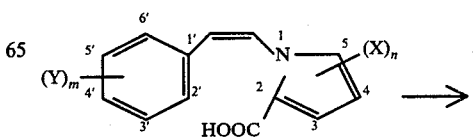

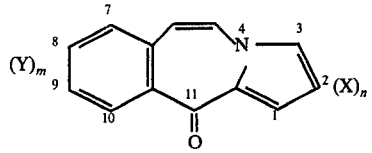

Table II

| Com- | Starting material | | Product | |
|---|---|---|---|---|
| pound | $(Y)_m$ | $(X)_n$ | $(Y)_m$ | $(X)_n$ |
| 1 | H | H | H (m.p. 113–114° C.) | H |
| 2 | H | 4-SCF$_3$ | H | 2-SCF$_3$ |
| 3 | 4'-Cl | H | 9-Cl (m.p. 206–208° C.)[a] | H |
| 4 | 4'-SCF$_3$ | H | 9-SCF$_3$ (m.p. 155–159° C.)* | H |
| 5 | 4'-CN | H | 9-CN (m.p. 213–217° C.)* | H |
| 6 | H | 4-COCH(CH$_3$)$_2$ | H | 2-COCH(CH$_3$)$_2$ |
| 7 | H | 4-SO$_2$N(CH$_3$)$_2$ | H | 2-SO$_2$N(CH$_3$)$_2$ |
| 8 | H | 4-SO$_2$CH(CH$_3$)$_2$ | H | 2-SO$_2$CH(CH$_3$)$_2$ |
| 9 | H | 4-Cl | H | 2-Cl |
| 10 | 4'-Br | H | 9-Br (m.p. 210–214° C. (dec.)) | H |
| 11 | H | 4-NO$_2$ | H | 2-NO$_2$ |
| 12 | 4'-OCH$_3$ | H | 9-OCH$_3$ | H |
| 13 | 4'-CF$_3$ | H | 9-CF$_3$ | H |
| 14 | 4'-Cl | 4-CN | 9-Cl (m.p. >220° C.)[b] | 2-CN |
| 15 | 4'-I | H | 9-I | H |
| 16 | 4'-F | H | 9-F | H |

[a]Used CH$_3$NO$_2$ and AlCl$_3$ in place of CH$_2$Cl$_2$ and SnCl$_4$.
[b]Used CH$_3$NO$_2$ and AlCl$_3$ at 0° C. on preformed acid chloride.
*m.p. of material made by a different route.

Example 2
2-Cyano-11H-pyrrolo[2,1-b][3]benzazepin-11-one

Step A: Preparation of trans-4-cyano-N-styrylpyrrole-2-carbonyl chloride

A mixture of 2.4 g. of trans-2-carboxy-4-cyano-N-styrylpyrrole (from Example 1) and 10 ml. of thionyl chloride was refluxed for 15 minutes, concentrated to dryness, treated with 10 ml. of toluene and concentrated to dryness to give 2.45 g. (95%) of trans-4-cyano-N-styrylpyrrole-2-carbonyl chloride, m.p. 119°–121° C.

Step B: Preparation of 4-cyano-N-(1,2-dichloro-2-phenylethyl)pyrrole-2-carbonyl chloride A solution of 256.5 mg. of trans-4-cyano-N-styrylpyrrole-2-carbonyl chloride in 5 ml. of chloroform was treated with 1 mmole of chlorine dissolved in 1 ml. of carbon tetrachloride. After 15 minutes, it was evaporated to dryness, treated with 5 ml. of carbon tetrachloride, and evaporated to dryness to give 307 mg. (94%) of oily 4-cyano-N-(1,2-dichloro-b 2-phenylethyl)pyrrole-2-carbonyl chloride.

Step C: Preparation of 2-cyano-5,6-dichloro-6,11-dihydro-5H-pyrrolo-[2,1-b][3]benzazapin-11-one Aluminum chloride (231 mg.) was added all at once to a mixture of 160 mg. of 4-cyano-N-(1,2-dichloro-2-phenylethyl)pyrrole-2-carbonyl chloride and 0.5 ml. of tetrachloroethane controlled at 140° C. After 4–5 minutes, the mixture is cooled, 15 ml. of water is added and the mixture is extracted with 4 × 10 ml. of chloroform. The extract is washed with water, dried and chromatographed on 10 g. of silica gel by elution with benzene:ethyl acetate (3:1 v/v). The first fraction provided 47 mg. (33%) of 2-cyano-5,6-dichloro-6,11-dihydro-5H-[2,1-b][3]benzazepin-11-one, m.p. 213°–223° C.

Step D: Preparation of 2-cyano-11H-pyrrolo[2,1-b][3]benzazepin-11-one

Chromous chloride prepared under nitrogen from 30 mg. of 100 mesh chromium and 0.1 ml. of concentrated hydrochloric acid in 0.4 ml. of water, was added to 20 mg. of 2-cyano-5,6-dichloro-6,11-dihydro-5H-pyrrolo[2,1-b][3]benzazepin-11-one in 0.1 ml. of acetone at 70° C. The mixture is poured into 5 ml. of water and extracted with 3 × 3 ml. of chloroform. The chloroform is washed with water, dried and concentrated to dryness to give 13 mg. (86%) of 2-cyano-11H-pyrrolo[2,1-b][3]benzazapin-11-one, m.p. 197° C.

Following the procedure substantially as described in Example 2 steps A, B, C, and D, but substituting for the trans-2-carboxy-4-cyano-N-styrylpyrrole used in step A thereof the trans-2-carboxy-N-styrylpyrroles described in Table I, there are produced in sequence the carbonyl chlorides, N-(1,2-dichloro-2-phenylethyl)pyrrole carbonyl chlorides, 5,6-dichloro-ketones, and 11H-pyrrolo[2,1-b][3]benzazepin-11-ones described in Table III by the following procedure:

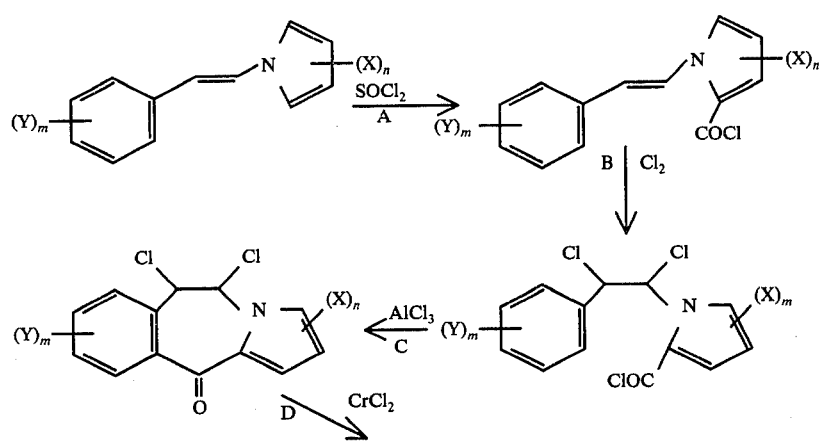

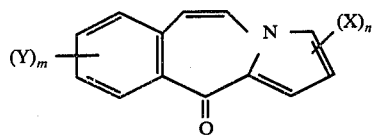

Table III

| (Y)$_m$ | (X)$_n$ |
|---|---|
| H | 2-Cl |
| H | 2-SO$_2$N(CH$_3$)$_2$ |
| H | 2-SO$_2$CH(CH$_3$)$_2$ |
| H | 2-NO$_2$ |
| H | 2-COCH(CH$_3$)$_2$ |
| H | 2-SO$_2$CH$_3$ |

Example 3

2-Cyano-11H-pyrrolo[2,1-b][3]benzazepin-11-one

Method I
Step A: Preparation of methyl 4-cyano-N-phenacylpyrrole-2-carboxylate

A mixture of 2 g. of methyl 4-cyanopyrrole-2-carboxylate, 2.7 g. of potassium carbonate, 2.7 g. of phenacylbromide and 15 ml. of dimethyl formamide was heated at 100° C. for 30 minutes. The mixture was poured into 200 ml. of water and extracted twice with ether. The extract was washed with water, dried and concentrated to dryness. The residue was triturated with petroleum ether to give 3 g. (84%) of methyl 4-cyano-N-phenacylpyrrole-2-carboxylate, m.p. 169°–172° C.

Step B: Preparation of 4-cyano-N-(2-chloro-2-phenethyl)-pyrrole-2-carbonyl chloride A mixture of 270 mg. of methyl 4-cyano-N-phenacylpyrrole-2-carboxylate, 0.2 ml. of 6N sodium hydroxide solution and 5 ml. of ethanol was refluxed for 1 hour and the mixture was concentrated to a dry residue of 298 mg.

The residue was taken up in 5 ml. of aqueous ethanol (1:1 v/v) and treated with 40 mg. of sodium borohydride at room temperature for 30 minutes. The mixture was concentrated to dryness.

The residue (351 mg.) was treated with 2 ml. of phosphorus oxychloride and 400 mg. of phosphorus pentachloride and heated at 110° C. for 18 hours. The mixture was concentrated to dryness, the residue was dissolved in 25 ml. of chloroform, washed with 2 × 20 ml. of water, dried and concentrated to dryness. The residue was chromatographed on 5 g. of silica gel by elution with benzene-ethylacetate (1:1 v/v). Concentration of the appropriate eluate provided 277 mg. of oily 4-cyano-N-(2-chloro-2-phenethyl)pyrrole-2-carbonyl chloride whose nmr and I.R. spectrum confirmed the structure.

Following the procedure substantially as described in Example 3, Method I, Steps A and B, but substituting for the starting material employed therein, equimolecular amounts of the methylpyrrole-2-carboxylates described in Table IV in Step A thereof, there are produced the N-(2-chloro-2-phenylethyl)pyrrole-2-carbonyl chlories also described in Table IV by the following process.

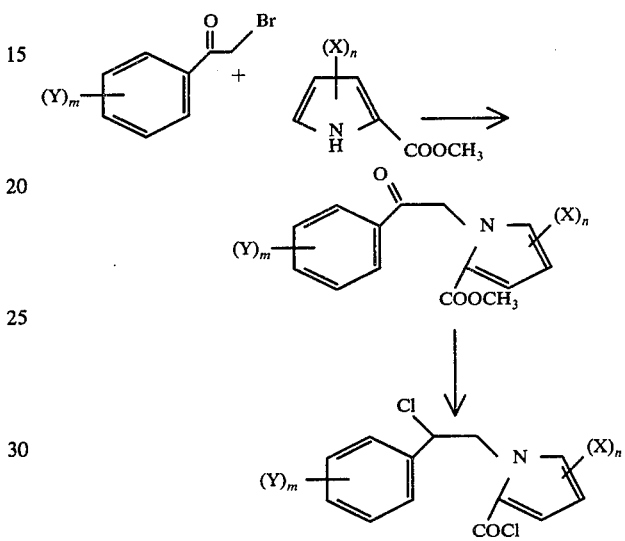

Table IV

| (Y)$_m$ | (X)$_n$ |
|---|---|
| H | 4-Cl |
| H | 4-SO$_2$N(CH$_3$)$_2$ |
| H | 4-SO$_2$CH(CH$_3$)$_2$ |
| H | 4-NO$_2$ |
| H | 4-COCH(CH$_3$)$_2$ |

Method II
Step A: Preparation of 4-cyano-N-(2-hydroxy-2-phenylethyl)pyrrole-2-carboxylic acid lactone Following the procedure of Example 1, Step A, but substituting for the sodium hydride employed therein, a catalytic amount of potassium t-butoxide, there is produced 4-cyano-N-(2-hydroxy-2-phenylethyl)pyrrole-2-carboxylic acid lactone.

Step B: Preparation of 4-cyano-N-(2-chloro-2-phenylethyl)pyrrole-2-carbonyl chloride A mixture of 0.54 g. of lactone from Example 3, Method II, Step A, 1 g. of phosphorus pentachloride and 5 ml. of phosphorus oxychloride is refluxed for 36 hours. The volatiles were removed in vacuo, and the residue was flushed three times by vacuum distillation of toluene to give 0.54 g. (93%) of 4-cyano-N-(2-chloro-2-phenylethyl)pyrrole-2-carbonyl chloride.

Following the procedure substantially as described in Example 3, Method B, Steps A and B but substituting for the methyl 4-cyanopyrrole-2-carboxylate used in Step A, thereof an equimolecular amount of the methyl pyrrole-2-carboxylates described in Table IV, there are produced the N-(2-chloro-2-phenylethyl)pyrrole-2-carbonyl chlorides also described in Table IV, by the following process:

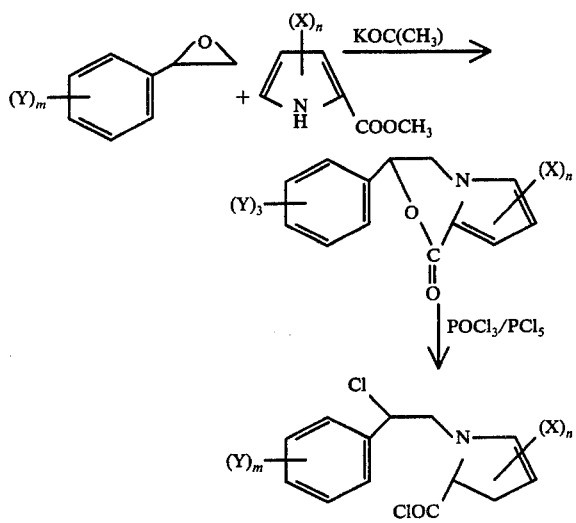

Step C: Preparation of 2-cyano-11H-pyrrolo[2,1-b][3]benzazepin-11-one

Following the procedure substantially as described in Example 2, Step C, but substituting for the starting material employed therein, an equimolecular amount of 4-cyano-N-(2-chloro-2-phenylethyl)pyrrole-2-carbonyl chloride, there is produced 6-chloro-2-cyano-6,11-dihydro-5H-pyrrolo[2,1-b][3]benzazepin-11-one. This material was dissolved in 5 ml. of ethanol containing 2 pellets of potassium hydroxide and refluxed for 15 minutes. The ethanol was evaporated. The residue was partitioned between water and chloroform. The chloroform was washed with water, dried and evaporated to dryness to give 109 mg. of crude product. This was chromatographed on 10 g. of silica gel by elution with benzene:ethyl acetate (3:1 v/v) to provide pure 2-cyano-11H-pyrrolo[2,1-b][3]benzazepin-11-one, m.p. 197° C.

Following the procedure of Example 3, Step C, but substituting for the starting material used therein an equimolecular amount of the carbonyl chlorides from Table IV, there are produced the ketones of Table V by the following process:

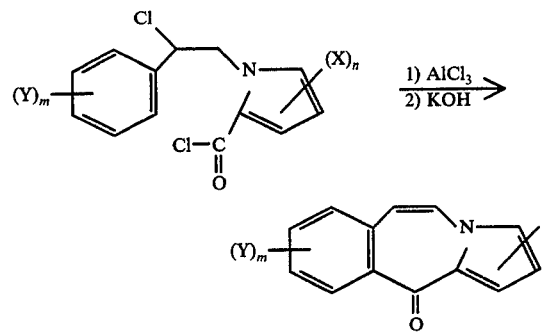

Table V

| (Y)$_m$ | (X)$_n$ |
|---|---|
| H | 2-Cl |
| H | 2-SO$_2$N(CH$_3$)$_2$ |
| H | 2-SO$_2$CH(CH$_3$)$_2$ |
| H | 2-NO$_2$ |
| H | 2-COCH(CH$_3$)$_2$ |

Example 4

3-Trifluoromethylthio-11H-pyrrolo[2,1-b][3]benzazepin-11-one

A mixture of 100 mg. of 11H-pyrrolo[2,1-b][3]-benzazepin-11-one, 100 mg. of pyridine, and 1.5 ml. of chloroform, and 1 meq. of trifluoromethylsulfenyl chloride after 200 minutes at 45° C. was poured into water. The organic phase was washed with dilute hydrochloric acid, water, dried and concentrated to dryness. The residue on recrystallization from ether gave 124 mg. of 3-trifluoromethylthio-11H-pyrrolo[2,1-b][3]benzazepin-11-one, m.p. 137°-137.5° C.

Example 5

2-Pentanoyl-11H-pyrrolo[2,1-b][3]benzazepin-11-one

11H-Pyrrolo[2,1-b][3]benzazepin-11-one (1.0 g.) is dissolved in 20 ml. of methylene chloride and 2.66 g. of aluminum chloride is added with cooling. At room temperature there is added little by little 720 mg. of pentanoyl chloride. Fifteen minutes after the addition is complete the mixture is poured onto ice. The organic phase is separated, filtered, dried and concentrated to dryness. The residue is triturated with ether, collected and dried to give 2-pentanoyl-11H-pyrrolo[2,1-b][3]benzazepin-11-one.

Employing the procedure substantially as described in Example 5, but substituting for the pentanoyl chloride used therein equimolecular amounts of isobutyryl chloride or dimethylsulfamoyl chloride, there are produced 2-isobutyroyl-11H-pyrrolo[2,1-b][3]benzazepin-11-one or 2-dimethyl-sulfamoyl-11H-pyrrolo-[2,1-b][3]benzazepin-11-one. In the latter case, the reaction is conducted in nitromethane at reflux temperature.

Following the procedure of Example 5, but conducting the reaction at 100°-130° C. with excess alkanoyl chloride as solvent and without the aluminum chloride, there are produced mixtures of 2- and 3-alkanoylketones which upon chromatographic separation on silica gel provides the alkanoyl ketone products described in Example 5 as well the corresponding 3-pentanoyl- and 3-isobutyroyl- compounds.

Example 6

2-Carbamoyl-11H-pyrrolo[2,1-b][3]benzazepin-11-one

2-Cyano-11H-pyrrolo[2,1-b][3]benzazepin-11-one (30 g., 0.135 mole) in 100 ml. of concentrated hydrochloric acid and 100 ml. of acetic acid is refluxed for 2 hours. It is then poured onto 500 ml. of water and continuously extracted with methylene chloride. The solution is left to cool to room temperature and filtered to afford 2-carbamoyl-11H-pyrrolo[2,1-b][3]benzazepin-11-one.

Example 7

2-Carboxy-11H-pyrrolo[2,1-b][3]benzazepine-11-one

To 2-carbamoyl-11H-pyrrolo[2,1-b][3]benzazepine-11-one (27 g., 0.112 moles) in 300 ml. of 50% sulfuric acid maintained at 50° C. is added slowly 25 g. of sodium nitrite in 75 ml. of water. At the end of the addition, the solid is filtered, washed with water and air-dried to yield 2-carboxy-11H-pyrrolo[2,1-b][3]benzazepine-11-one.

Example 8

2-Dimethylcarbamoyl-11H-pyrrolo[2,1-b][3]benzazepin-11-one

Step A: Preparation of 2-chlorocarbonyl-11H-pyrrolo[2,1-b][3]benzazepin-11-one 11H-11-oxo-pyrrolo[2,1-b][3]benzazepine-2-carboxylic acid (24 g., 99 mmoles) in 100 ml. of thionyl chloride is refluxed for 15 minutes. The volatiles are removed under vacuum and the residue is triturated in ether. Filtration and air drying yields 2-chlorocarbonyl-11H-pyrrolo[2,1-b][3]benzazepin-11-one.

Step B: Preparation of 2-dimethylcarbamoyl-11H-pyrrolo[2,1-b][3]benzazepine-11-one Anhydrous dimethyl amine is bubbled through a suspension of 2-chlorocarbonyl-11H-pyrrolo[2,1-b][3]benzazepin-11-one (23 g., 88.5 mmoles) in 100 ml. of methylene chloride. (Note: The introduction of dimethyl amine causes the mixture to reflux and this reflux stops when all the acid chloride is reacted.)

The reaction mixture is washed with water and dried over sodium sulfate. It is then taken to dryness, triturated in ether, filtered and air-dried to yield 2-dimethylcarbamoyl-11H-pyrrolo[2,1-b][3]benzazepin-11-one.

Following the procedure of Example 8, Step B, but substituting for the dimethylamine used therein, an equimolecular amount of methylamine, there is produced 2-methylcarbamoyl-11H-pyrrolo[2,1-b][3]benzazepin-11-one.

Example 9

2-Methoxycarbonyl-11H-pyrrolo[2,1-b][3]benzazepin-11-one

11-Oxo-11H-pyrrolo[2,1-b][3]benzazepine-2-carboxylic acid (25.5 g., 0.11 moles) in 300 ml. of methanol saturated with hydrogen chloride is refluxed until a homogeneous solution is obtained (4 hours).

The volatiles are removed under vacuum and the residue is dissolved in 300 ml. of methylene chloride, washed with dilute sodium hydroxide and then with water. It is dried over sodium sulfate and concentrated. The residue is triturated in ether, filtered and air-dried, to yield 2-methoxycarbonyl-11H-pyrrolo[2,1-b][3]benzazepine-11-one.

Example 10

9-Trifluoromethylthio-11H-pyrrolo[2,1-b][3]benzazepin-11-one

A mixture of 42.56 g. of bis(trifluoromethylthio)mercury, 17.27 g. of 9-bromo-11H-pyrrolo[2,1-b][3]benzazepin-11-one, 28 g. of electrolytic copper dust, 98 ml. of quinoline and 84 ml. of pyridine is stirred and heated at 195° C. for 18 hours. The mixture is shaken with 400 ml. of 6N hydrochloric acid and 400 ml. benzene. The organic phase is washed with 5 × 300 ml. of 3N hydrochloric acid and 5 × 300 ml. of water, dried over magnesium sulfate, filtered and concentrated to dryness, to give 9-trifluoromethylthio-11H-pyrrolo[2,1-b][3]benzazepin-11-one, m.p. 155°–159° C.

Example 11

Preparation of 2-formyl-11H-pyrrolo[2,1-b][3]benzazepin-11-one

2-Cyano-11H-pyrrolo[2,1-b][3]benzazepin-11-one (222 mg.) and 222 mg. nickel-aluminum alloy in 2 ml. 75% formic acid is refluxed for 1½ hours. The solid is filtered off and washed with ethanol. The filtrate is diluted with 50 ml. water and extracted twice with 50 ml. methylene chloride. The organic layer is washed with water, 5% sodium bicarbonate and with water; it is then dried over magnesium sulfate and evaporated to dryness. Addition of ether induces crystallization and the crystals are filtered and air-dried to yield 2-formyl-11H-pyrrolo[2,1-b][3]benzazepin-11-one.

Using substantially the procedure described in Example 11, but starting with 9-cyano-11H-pyrrolo[2,1-b][3]benzazepin-11-one in place of the 2-cyano compound, there is obtained 9-formyl-11H-pyrrolo[2,1-b][3]benzazepin-11-one.

Example 12

9-Cyano-11H-pyrrolo[2,1-b][3]benzazepin-11-one

A stirred mixture of 1 gm. of 9-bromo-11H-pyrrolo[2,1-b][3]benzazepin-11-one, 1 gm. of cuprous cyanide and 5 ml. of dimethylformamide is heated to reflux for 5 hr. The mixture is then poured into a solution of 4 gm. of ferric chloride hydrate in 25 ml. of 2N hydrochloric acid. After stirring the resulting mixture at 60° for 30 min., it is extracted with 3 × 50 ml. of ethyl acetate, the organic extracts washed with 3 × 100 ml. of water and dried over $Na_2SO_4$. Evaporation of the dried solution yields 9-cyano-11H-pyrrolo[2,1-b][3]benzazepin-11-one, m.p. 213°–217° C.

Example 13

2-Hydroxymethyl-11H-pyrrolo[2,1-b][3]benzazepin-11-one

A solution of 2.23 gm. of 2-formyl-11H-pyrrolo[2,1-b][3]benzazepin-11-one and 95 mg. of sodium borohydride in 20 ml. of ethanol is stirred at 25° C. for 2 hrs. The solvent is evaporated and the residue dissolved in methylene chloride to extract the crude product from inorganic materials. After chromatography on silica gel, there is obtained 2-hydroxymethyl-11H-pyrrolo[2,1-b][3]benzazepin-11-one.

Example 14

2-Trifluoromethyl-11H-pyrrolo[2,1-b][3]benzazepin-11-one

In a sealed Hasteloy-C lined pressure vessel a mixture of 10 gm. of 2-carboxy-11H-pyrrolo[2,1-b][3]benzazepin-11-one and 15 gm. of sulfur tetrafluoride is heated at 100° for 4 hrs., then at 130° for 4 hrs. The vessel is cooled to room temperature and opened cautiously (toxic fumes!). The contents of the vessel are extracted with 300 ml. of ether and the ether solution stirred vigorously with 200 ml. of 1N sodium hydroxide for 6 hrs. The ether layer is separated, dried and evaporated and the residue chromatographed over silica gel to yield 2-trifluoromethyl-11H-pyrrolo[2,1-b][3]benzazepin-11-one.

Example 15

9-Methylthio-11H-pyrrolo[2,1-b][3]benzazepin-11-one

A mixture of 27 gm. of 9-bromo-11H-pyrrolo[2,1-b][3]benzazepin-11-one, 15 gm. of cuprous methylsulfide, 170 ml. of quonoline and 15 ml. of pyridine is stirred under a nitrogen atmosphere for 6 hrs. at a temperature of 195° C. The reaction mixture is cooled and poured into 500 ml. of 6N HCl containing 300 gm. of cracked ice. The resulting mixture is extracted with 3 × 200 ml. of benzene which is then filtered to remove some insoluble black material. The benzene extracts are washed with 3N HCl until the aqueous layer remains acidic, then washed with 100 ml. $H_2O$, dried $(Na_2SO_4)$ and evaporated to yield 9-methylthio-11H-pyrrolo[2,1-b][3]benzazepin-11-one.

Following the above procedure of Example 15 but replacing cuprous methylsulfide by cuprous isopropylsulfide, there is obtained 9-isopropylthio-11H-pyrrolo[2,1-b][3]benzazepin-11-one.

Example 16

2-Trifluoromethylsulfinyl-11H-pyrrolo[2,1-b][3]benzazepin-11-one

A solution of 3 gm. of 2-trifluoromethylthio-11H-pyrrolo[2,1-b][3]benzazepin-11-one in 25 ml. of acetic acid containing 3 ml. of 50% hydrogen peroxide is stirred at 25° C. for 6 hrs. The solvent is evaporated and the residue dissolved in 100 ml. of methylene chloride. The solution is washed with 2 × 25 ml. of 5% $Na_2CO_3$ solution, dried and evaporated. Chromatography of the residue on silica gel yields 2-trifluoromethylsulfinyl-11H-pyrrolo[2,1-b][3]benzazepin-11-one.

Using the procedure of Example 16 but starting with 9-methylthio-11H-pyrrolo[2,1-b][3]benzazepin-11-one, there is obtained 9-methylsulfinyl-11H-pyrrolo[2,1-b][3]benzazepin-11-one.

Similarly, 9-isopropylthio-11H-pyrrolo[2,1-b][3]benzazepin-11-one, using the procedure of Example 16, produces 9-isopropylsulfinyl-11H-pyrrolo[2,1-b][3]benzazepin-11-one.

Example 17

2-Trifluoromethylsulfonyl-11H-pyrrolo[2,1-b][3]benzazepin-11-one

A solution of 2 gm. of 2-trifluoromethylsulfinyl-11H-pyrrolo[2,1-b][3]benzazepin-11-one in 20 ml. of acetic acid containing 5 ml. of 90% hydrogen peroxide is stirred at 25° C. for 4 days. The solvent is evaporated and the residue dissolved in 100 ml. of methylene chloride. After washing the organic solution with 2 × 25 ml. of 1N $Na_2CO_3$, it is dried and evaporated, and the residue chromatographed on silica gel to yield 2-trifluoromethylthio-11H-pyrrolobenzazepin-11-one.

Using the procedure of Example 17 but starting with 9-methylsulfinyl-11H-pyrrolo[2,1-b][3]benzazepin-11-one there is prepared 9-methylsulfonyl-11H-pyrrolo[2,1-b][3]benzazepin-11-one.

Similarly using the procedure of Example 17 but starting with 9-isopropylsulfinyl-11H-pyrrolo[2,1-b][3]benzazepin-11-one there is obtained 9-isopropylsulfonyl-11H-pyrrolo[2,1-b][3]benzazepin-11-one.

Example 18

9-Hydroxy-11H-pyrrolo[2,1-b][3]benzazepin-11-one

Ethanethiol (0.62 g., 10 mmoles), dissolved in dimethyl formamide (10 ml.) is added to a suspension of sodium hydride (0.5 g. of 50% oil dispersion) in dry dimethyl formamide (5 ml.). The mixture is stirred until all hydrogen has evolved and 9-methoxy-11H-pyrrolo[2,1-b][3]benzazepin-11-one (2.26 g., 10 mmoles) is added. The solution is refluxed for a period of 3 hours. The cooled reaction mixture is acidified with 0.2N HCl and extracted with chloroform. The organic layer is washed with water, dried over sodium sulfate and concentrated to yield 9-hydroxy-11H-pyrrolo[2,1-b][3]benzazepin-11-one.

Example 19

9-Carbamoyl-11H-pyrrolo[2,1-b][3]benzazepin-11-one

9-Cyano-11H-pyrrolo[2,1-b][3]benzazepin-11-one (30 g., 0.135 mole) in 100 ml. of concentrated hydrochloric acid and 100 ml. of acetic acid is refluxed for 2 hours. It is then poured onto 500 ml. of water and continuously extracted with methylene chloride. The solution is left to cool to room temperature and filtered to afford 9-carbamoyl-11H-pyrrolo[2,1-b][3]benzazepin-11-one.

Example 20

9-Carboxy-11H-pyrrolo[2,1-b][3]benzazepin-11-one

To 9-carbamoyl-11H-pyrrolo[2,1-b][3]benzazepin-11-one (27 g., 0.112 moles) in 300 ml. of 50% sulfuric acid maintained at 50° C. is added slowly 25 g. of sodium nitrite in 75 ml. of water. At the end of the addition, the solid is filtered, washed with water and air-dried to yield 9-carboxy-11H-pyrrolo[2,1-b][3]benzazepin-11-one.

Example 21

9-Ethoxycarbonyl amino-11H-pyrrolo[2,1-b][3]benzazepin-11-one

To 9-carboxy-11H-pyrrolo[2,1-b][3]benzazepin-11-one (96 g., 0.4 moles) in 500 ml. ethanol, and is added successively triethylamine (52 g., 0.52 moles) and diphenylphosphoro azide (112 g., 0.40 mmoles). Reflux is maintained for 3 hrs. The mixture is poured onto water, extracted with ethyl acetate, washed with 1N sodium hydroxide and dried over magnesium sulfate to yield after evaporation 1.70 g. of a residue that is chromatographed on silica gel. Elution with methylene chloride yields 9-ethoxycarbonylamino-11H-pyrrolo[2,1-b][3]benzazepin-11-one.

Example 22

9-Amino-11H-pyrrolo[2,1-b][3]benzazepin-11-one

To 9-ethoxycarbonyl amino-11H-pyrrolo[2,1-b][3]benzazepin-11-one (2.80 g., 10 mmole) in 100 ml. EtOH is added 10 ml. 2N potassium hydroxide. Reflux is maintained for 42 hrs. The volatiles are removed under vacuum and the residue is extracted with chloroform, washed with water and dried over magnesium sulfate. Evaporation leaves a dark residue that is purified by chromotography on silica gel. Elution with 10% methanol in chloroform yields 9-amino-11H-pyrrolo[2,1-b][3]benzazepin-11-one that decomposes slowly on standing.

Example 23

9-Methylamino-11H-pyrrolo[2,1-b][3]benzazepin-11-one

A solution of 9-amino-11H-pyrrolo[2,1-b][3]benzazepin-11-one in triethyl orthoformate (2.17 g., 10 mmoles in 80 ml.) is refluxed for 5 hrs. The volatiles are removed under vacuum and the residue, dissolved in 100 ml. absolute ethanol is stirred in an ice bath as sodium borohydride (0.88 g., 0.024 moles) is added over a period of 10 minutes. The mixture is stirred for a period of 2 hrs. After concentration of the ethanol, the residue is dissolved in ethyl acetate, washed with water, dried over $Na_2SO_4$ and concentrated to dryness to yield 9-methylamino-11H-pyrrolo[2,1-b][3]benzazepin-11-one as a brown amorphous solid.

Example 24

9-Dimethylamino-11H-pyrrolo[2,1-b][3]benzazepin-11-one

To a solution of 9-amino-11H-pyrrolo[2,1-b][3]benzazepin-11-one (2.1 g., 10 mmoles) and 4 ml. (50 mmole) of 37% aqueous formaldehyde in 15 ml. of acetonitrile is added 1 g. (16 mmoles) of sodium cyano borohydride. A vigorous and exothermic reaction takes place and a dark residue separates. The mixture is stirred for 15 mins. and then glacial acetic acid is added dropwise until the solution tests neutral on wet pH paper. Stirring is maintained for an additional 2 hrs. The volatiles are removed under vacuum, and the residue is dissolved in chloroform. The solution is washed with base and with water, dried over sodium sulfate, and concentrated to leave a residue that is purified by chromatography on silica gel. Elution with chloroform yields 9-dimethylamino-11H-pyrrolo[2,1-b][3]benzazepin-11-one as a dark brown oil.

Example 25

9-Acetamido-11H-pyrrolo[2,1-b][3]benzazepin-11-one

9-Amino-11H-pyrrolo[2,1-b][3]benzazepin-11-one (2.1 g., 11.4 mmoles) dissolved in 15 ml. pyridine is treated with acetic anhydride (2 ml.) at room temperature for 19 hours. The volatiles are removed under vacuum and the residue is dissolved in chloroform, and chromatographed on silica gel. Elution with chloroform yields 9-acetamido-11H-pyrrolo[2,1-b][3]benzazepin-11-one.

The following Examples illustrate the preparation of the 11-($R^1R^2$-aminopropylidene)-pyrrolo[2,1-b][3]benzazepines of this invention and are not meant to limit the invention to the particular processes or novel compounds described therein.

Example I 11-(3-dimethylaminopropylidene)-6,11-dihydro-5H-pyrrolo[2,1-b][3]benzazepine Step A: Preparation of 11-Hydroxy-11-(3-dimethylaminopropyl)-6,11-dihydro-5H-pyrrolo[2,1-b][3]benzazepine To a solution of 16 g., (0.081 mole) of 6,11-dihydro-5H-pyrrolo[2,1-b][3]benzazepin-11-one in 300 ml. tetrahydrofuran (THF) is added 150 ml. of 1.0N solution of 3-dimethylaminopropyl magnesium chloride in THF. After stirring for 40 minutes at ice-bath temperature and for 1.5 hours at 25° C., the bulk of the solvent is distilled below 45° C. under reduced pressure. The residue is dissolved in 500 ml. of methylene chloride and the Grignard adduct is hydrolyzed by the dropwise addition of 15 ml. water with cooling in an ice bath. The methylene chloride solution is decanted and the gelatinous precipitate is extracted three times with 80 ml. portions of boiling benzene. The combined organic extracts are washed with water and then evaporated under reduced pressure to yield, after crystallization from ethanol, 11-hydroxy-11-(3-dimethylaminopropyl)-6,11-dihydro-5H-pyrrolo-[2,1-b][3]benzazepine, m.p. 68°-70° C.

Step B: Preparation of 11-(3-Dimethylaminopropylidene)-6,11-dihydro-5H-pyrrolo[2,1-b][3]benzazepine Hydrogen chloride gas is bubbled through a solution of 4.8 gm. (0.017 moles) of 11-hydroxy-11-(3-dimethylaminopropyl)-6,11-dihydro-5H-pyrrolo[2,1-b][3]benzazepine in 70 ml. of chloroform at 0° C. for 5 minutes. The resulting dark mixture is stirred for an additional 5 minutes, and then washed with 6M NaOH to provide, after evaporation of the chloroform, 4.3 g. of 11-(3-dimethylaminopropylidene)-6,11-dihydro-5H-pyrrolo[2,1-b][3]benzacepine as an oil. It is converted to a crystalline oxalate by adding a solution of 266 mg. of the free base in 5 ml. of ethanol to a mixture of 90 mg. of oxalic acid and 2 ml. of ethanol and collecting the precipitate by filtration and air drying; m.p. 140°-165° C. (dec.).

Following the procedure of Example I, Step B, there may be substituted for the hydrogen chloride-chloroform system (1) used therein trifluoroacetic anhydride-chloroform (2), trifluoroacetic acid (3), oxalic acid in ethanol (4), phosphorus oxychloride-pyridine (5), trichloroacetic acid-ethanol (6), acetic acid (7), or formic acid (8).

Following the procedure of Example I, Steps A and B, but substituting for the 6,11-dihydro-5H-pyrrolo[2,1-b][3]benzazepin-11-one used in Step A thereof an equimolecular amount of the ketones described in Table A, there are produced in sequence the 11-hydroxy-11-(3-$R_a^1$,$R_a^2$-aminopropyl)-6,11-dihydro-5H-pyrrolo[2,1-b][3]benzazepines and 11-(3-$R_a^1$,$R_a^2$-aminopropylidene)-6,11-dihydro-5H-pyrrolo[2,1-b][3]benzazepines also described in Table A in accordance with the following process:

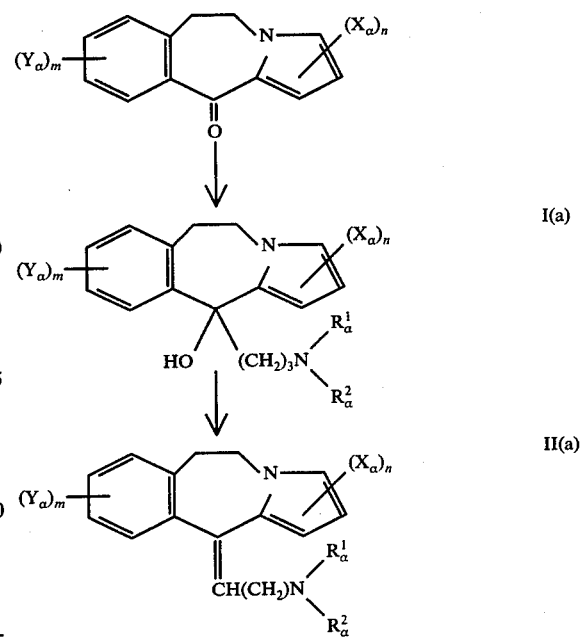

TABLE A

| $R_a^1$ | $R_a^2$ | $(Y_a)_m$ | $(X_a)_n$ | Dehydrating Agent | M.P.(° C.) Oxalate Salt of Compound II(a) |
|---|---|---|---|---|---|
| CH₃ | CH₃ | H | 2-SO₂N(CH₃)₂ | 1 | 128-136 |
| CH₃ | CH₃ | H | 2-CN | 1 | 211-215 |
| CH₃ | CH₃ | H | 2-CO₂CH₃ | 1 | 115 (dec.) |
| CH₃ | CH₃ | H | 2-Cl | 1 | 142-160 |
| CH₃ | CH₃S | H | 2-CO₂H | 1 | 223-231 (dec.)* |
| CH₃ | CH₃ | H | 2-SCF₃ | 1 | 161 (dec.) |
| CH₃ | CH₃ | H | 3-SCF₃ | 1 | 174 (dec.) |
| CH₃ | CH₃ | H | 2-CON(CH₃)₂ | 1 | 167 (dec.) |
| CH₃ | CH₃ | H | 3-CF₃ | 1 | 155-159 |

TABLE A-continued

| $R_a^1$ | $R_a^2$ | $(Y_a)_m$ | $(X_a)_n$ | Dehydrating Agent | M.P.(° C.) Oxalate Salt of Compound II(a) |
|---|---|---|---|---|---|
| CH$_3$ | CH$_3$ | H | 2-COCH(CH$_3$)$_2$ | 1 | 120–125 |
| CH$_3$ | CH$_3$ | H | 2-CO(CH$_2$)$_3$CH$_3$ | 1 | 115–132 (dec.) |
| CH$_3$ | CH$_3$ | H | 2-SO$_2$CH$_3$ | 1 | 155–158 |
| CH$_3$ | CH$_3$ | H | 2-SO$_2$CH(CH$_3$)$_2$ | 1 | |
| CH$_3$ | CH$_3$ | H | 2-SO$_2$CF$_3$ | 2 | |
| CH$_3$ | CH$_3$ | H | 2-CO$_2$C$_2$H$_5$ | 1 | |
| CH$_3$ | CH$_3$ | H | 2-NO$_2$ | 3 | |
| CH$_3$ | CH$_3$ | H | 2-COCH$_3$ | 1 | 150–165 (dec.) |
| CH$_3$ | CH$_3$ | H | 2-CF$_3$ | 1 | |
| CH$_3$ | CH$_3$ | 9-OCONHCH$_3$ | 2,3-Br$_2$ | 4 | |
| CH$_3$ | CH$_3$ | 9-NHCOOCH$_3$ | 2,3-Br$_2$ | 4 | |
| CH$_3$ | CH$_3$ | 9-CH$_3$ | 2,3-Br$_2$ | 7 | |
| CH$_3$ | CH$_3$ | H | 2,3-Br$_2$ | 1 | 180–185 (dec.) |
| CH$_3$ | CH$_3$ | H | 2-Br | 4 | |
| CH$_3$ | CH$_3$ | H | 3-CN | 4 | 180–185 (dec.) |
| CH$_3$ | CH$_3$ | H | 1,2,3-Br$_3$ | 5 | |
| CH$_3$ | CH$_3$ | H | 1,3-Br$_2$-2-CH$_3$ | 6 | |
| CH$_3$ | CH$_3$ | 9-NHCOCH$_3$ | 1,2,3-Br$_3$ | 1 | |
| CH$_3$ | CH$_3$ | 9-CH(CH$_3$)$_2$ | 2,3-Br$_2$ | 4 | |
| CH$_3$ | CH$_3$ | 9-SCH$_3$ | 2,3-Br$_2$ | 4 | |
| CH$_3$ | CH$_3$ | 8,9-(CH$_3$)$_2$ | 2-CN | 7 | |
| CH$_3$ | CH$_3$ | 9-OH | 2-CN | 4 | |
| CH$_3$ | CH$_3$ | 9-OCH$_3$ | 2-CN | 4 | |
| CH$_3$ | CH$_3$ | H | 2,3-Cl$_2$ | 5 | |
| CH$_3$ | CH$_3$ | 9-OCONHCH$_3$ | H | 4 | |
| CH$_3$ | CH$_3$ | 9-NHCOOCH$_3$ | H | 4 | |
| CH$_3$ | CH$_3$ | 9-CH$_3$ | H | 4 | 127–130 |
| CH$_3$ | CH$_3$ | 9-CH(CH$_3$)$_2$ | H | 4 | |
| CH$_3$ | CH$_3$ | H | 2-CH$_3$ | 7 | |
| CH$_3$ | CH$_3$ | 9-NHCOCH$_3$ | H | 4 | 160–170 (dec.) |
| CH$_3$ | CH$_3$ | 9-SCH$_3$ | H | 4 | |
| CH$_3$ | CH$_3$ | 9-SCH(CH$_3$)$_2$ | H | 4 | |
| CH$_3$ | CH$_3$ | H | 3-CO(CH$_2$)$_4$H | 1 | |
| CH$_3$ | CH$_3$ | H | 3-COCH$_3$ | 1 | |
| CH$_3$ | CH$_3$ | H | 3-COCH(CH$_3$)$_2$ | 1 | |
| CH$_3$ | CH$_3$ | 9-I | H | 4 | |
| CH$_3$ | CH$_3$ | 9-SCF$_3$ | H | 4 | 155–165 (dec.) |
| CH$_3$ | CH$_3$ | 9-NO$_2$ | H | 1 | |
| CH$_3$ | CH$_3$ | 9-NH$_2$ | | 1 | |
| CH$_3$ | CH$_3$ | 9-NHCH$_3$ | H | 1 | |
| CH$_3$ | CH$_3$ | 9-N(CH$_3$)$_2$ | H | 1 | |
| CH$_3$ | CH$_3$ | 9-CN | H | 8 | 175–177 (dec.) |
| CH$_3$ | CH$_3$ | 9-SOCF$_3$ | H | 4 | |
| CH$_3$ | CH$_3$ | 9-SOCH$_3$ | H | 4 | |
| CH$_3$ | CH$_3$ | 9-SOCH(CH$_3$)$_2$ | H | 4 | |
| CH$_3$ | CH$_3$ | 9-SO$_2$CF$_3$ | H | 1 | |
| CH$_3$ | CH$_3$ | 9-SO$_2$CH$_3$ | H | 1 | |
| CH$_3$ | CH$_3$ | 9-SO$_2$CH(CH$_3$)$_2$ | H | 1 | |
| CH$_3$ | CH$_3$ | 9-Cl | H | 4 | 160–165 (dec.) |
| CH$_3$ | CH$_3$ | 9-SCH(CH$_3$)$_2$ | H | 7 | |
| C$_2$H$_5$ | CH$_3$ | H | 2-CN | 1 | |
| —(CH$_2$)$_4$— | | H | H | 4 | |
| —(CH$_2$)$_5$— | | H | 2-CO(CH$_2$)$_3$CH$_3$ | 1 | |
| —(CH$_2$)$_2$O(CH$_2$)$_2$— | | 9-CN | H | 1 | |
| ◁ | CH$_3$ | H | 2-CN | 1 | |
| —CH$_2$C=CH$_2$ | —CH$_2$CH=CH$_2$ | H | 2-CN | 1 | |
| CH$_3$ | CH$_3$ | 9-CF$_3$ | H | 1 | |
| CH$_3$ | CH$_3$ | H | 3-SO$_2$CH$_3$ | 1 | 200–204 |
| CH$_3$ | CH$_3$ | H | 2-SOCH$_3$ | 1 | 142–147 |
| CH$_3$ | CH$_3$ | 9-Br | H | 4 | |
| CH$_3$ | CH$_3$ | 9-F | H | 4 | |

*hydrochloride salt

EXAMPLE II

2-Cyano-11-(3-dimethylaminopropylidene)-11H-pyrrolo[2,1-b][3]benzazepine

Step A: Preparation of 2-Cyano-11-(3-dimethylaminopropyl)11-hydroxy-11H-pyrrolo[2,1-b][3]benzazepine A mixture of 4 g. of 2-cyano-11H-pyrrolo[2,1-b][3]benzazepin-11-one in 50 ml. of tetrahydrofuran is treated dropwise with 20 ml. of tetrahydrofuran containing 28.40 mmole of 3-(dimethylamino)propylmagnesium chloride while maintaining the temperature at 25° C. Ten minutes after the addition is complete, 2 ml. of water is added and the mixture is poured into 200 ml. of methylene chloride, dried over sodium sulfate and filtered. Concentration to dryness provides 3.3 g. (60%) of a solid residue of 2-cyano-11-(3-dimethylaminopropyl)-11-hydroxy-11H-pyrrolo[2,1-b][3]benzazepine, m.p. 123°–126° C.

Step B: Preparation of 2-Cyano-11-(3-dimethylaminopropylidene)-11H-pyrrolo[2,1-b][3]benzazepine A mixture of 2.8 g. of the 11-hydroxy compound in 50 ml. of chloroform is treated with hydrogen chloride gas for 5 minutes while maintaining the temperature at 25° C. The mixture is neutralized with 2N sodium hydroxide and extracted twice with chloroform. The extract is washed with water, dried and concentrated to dryness to give 2.4 g. of oil.

The oil is dissolved in 10 ml. of acetonitrile and treated with 1.0 g. of oxalic acid. After 4 hours at room temperature and overnight in the refrigerator, the solids are collected, washed with ether and air dried to give 2.7 g. of 2-cyano-11-(3-dimethylaminopropylidene)-11H-pyrrolo[2,1-b][3]benzazepine, oxalate, m.p. 185°–187° C.

Following the procedure of Example II, Step B, there may be substituted for the hydrogen chloride-chloroform system (1) used therein, trifluoroacetic anhydride-chloroform (2), trifluoroacetic acid (3), oxalic acid in ethanol (4), phosphorus oxychloride-pyridine (5), trichloroacetic acid-ethanol (6), acetic acid (7), or formic acid (8).

Following the procedure of Example II, Steps A and B, but substituting for the 2-cyano-11H-pyrrolo[2,1-b][3]benzazepin-11-one used in Step A thereof an equimolecular amount of the ketones described in Table B, there are produced in sequence the 11-hydroxy-11-(3-$R_\alpha^1,R_\alpha^2$-aminopropyl11H-pyrrolo[2,1-b][3]benzazepines and 11-(3-$R_\alpha^1,R_\alpha^2$-aminopropylidene)-11H-pyrrolo[2,1-b][3]benzazepines also described in Table B in accordance with the following process:

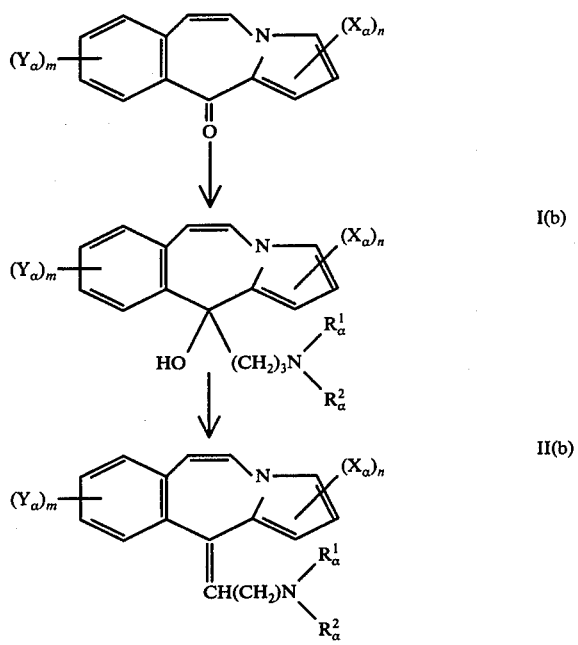

TABLE B

| $R_\alpha^1$ | $R_\alpha^2$ | $(Y_\alpha)_m$ | $(X_\alpha)_m$ | Dehydrating Agent | M.P.(° C.) Oxalate Salt of Compound II(a) |
|---|---|---|---|---|---|
| CH$_3$ | CH$_3$ | H | H | 4 | 100 (dec.) |
| CH$_3$ | CH$_3$ | H | 2-SCF$_3$ | 4 | |
| CH$_3$ | CH$_3$ | 9-Cl | H | 5 | 185–188 (dec.) |
| CH$_3$ | CH$_3$ | 9-SCF$_3$ | H | 4 | 110 (dec.) |
| CH$_3$ | CH$_3$ | 9-CN | H | 8 | 157–160 (dec.) |
| CH$_3$ | CH$_3$ | H | 2-COCH(CH$_3$)$_2$ | 1 | |
| CH$_3$ | CH$_3$ | H | 2-SO$_2$N(CH$_3$)$_2$ | 1 | |
| CH$_3$ | CH$_3$ | H | 2-SO$_2$CH(CH$_3$)$_2$ | 1 | |
| CH$_3$ | CH$_3$ | H | 2-Cl | 1 | |
| CH$_3$ | CH$_3$ | 9-Br | H | 4 | |
| CH$_3$ | CH$_3$ | H | 2-NO$_2$ | 3 | |
| CH$_3$ | CH$_3$ | 9-OCH$_3$ | H | 4 | |
| CH$_3$ | CH$_3$ | H | 3-SCF$_3$ | 1 | |
| CH$_3$ | CH$_3$ | H | 2-CO(CH$_2$)$_3$CH$_3$ | 1 | |
| CH$_3$ | CH$_3$ | H | 3-CO(CH$_2$)$_3$CH$_3$ | 1 | |
| CH$_3$ | CH$_3$ | H | 3-COCH(CH$_3$)$_2$ | 1 | |
| CH$_3$ | CH$_3$ | H | 2-CON(CH$_3$)$_2$ | 1 | |
| CH$_3$ | CH$_3$ | H | 2-COOCH$_3$ | 1 | |
| CH$_3$ | CH$_3$ | H | 2-CH$_2$OH | 7 | |
| CH$_3$ | CH$_3$ | H | 2-CF$_3$ | 1 | |
| CH$_3$ | CH$_3$ | 9-SCH$_3$ | H | 4 | |
| CH$_3$ | CH$_3$ | 9-SCH(CH$_3$)$_2$ | H | 4 | |
| CH$_3$ | CH$_3$ | H | 2-SOCF$_3$ | 4 | |
| CH$_3$ | CH$_3$ | 9-SOCH$_3$ | H | 4 | |
| CH$_3$ | CH$_3$ | 9-SOCH(CH$_3$)$_2$ | H | 4 | |
| CH$_3$ | CH$_3$ | H | 2-SO$_2$CF$_3$ | 2 | |
| CH$_3$ | CH$_3$ | 9-SO$_2$CH$_3$ | H | 1 | |
| CH$_3$ | CH$_3$ | 9-SO$_2$CH(CH$_3$)$_2$ | H | 1 | |
| CH$_3$ | CH$_3$ | 9-OH | H | 4 | |
| CH$_3$ | CH$_3$ | 9-COOC$_2$H$_5$ | | 1 | |
| CH$_3$ | CH$_3$ | 9-NH$_2$ | H | 1 | |
| CH$_3$ | CH$_3$ | 9-NHCH$_3$ | H | 1 | |
| CH$_3$ | CH$_3$ | 9-N(CH$_3$)$_2$ | H | 1 | |
| CH$_3$ | CH$_3$ | 9-NHCOCH$_3$ | H | 4 | |
| C$_2$H$_5$ | CH$_3$ | H | 2-CN | 1 | |
| —(CH$_2$)$_4$— | | H | H | 4 | |
| —(CH$_2$)$_5$— | | H | 2-CO(CH$_2$)$_3$CH$_3$ | 1 | |
| —(CH$_2$)$_2$O(CH$_2$)$_2$— | | 9-CN | H | 8 | |
| CH$_3$ | CH$_3$ | H | 2-SO$_2$CH$_3$ | 1 | |
| CH$_3$ | CH$_3$ | 9-CF$_3$ | H | 1 | |
| CH$_3$ | CH$_3$ | 9-Cl | 2-CN | 1 | 217–219 (dec.) |
| CH$_3$ | CH$_3$ | 9-I | H | 4 | |
| CH$_3$ | CH$_3$ | 9-F | H | 4 | |

EXAMPLE III

2-Formyl-11-(3-dimethylaminopropylidene)-6,11-dihydro-5H-pyrrolo[2,1-b][3]benzazepine 2-Cyano-11-(3-dimethylaminopropyl)-11-hydroxy-6,11-dihydro-5H-pyrrolo[2,1-b][3]benzazepine (.62 g.) and 6.2 g. Ni-Al 1:1 alloy powder (BDH Chemicals Ltd., Pool England) in 50 ml. 75% formic acid is refluxed for 1 hr. The dark red suspension is cooled, filtered to remove the insolubles, washed with formic acid and evaporated to dryness. The yield of this red oil is 3.4 g. (57%) and it slowly crystallizes on cooling. The oxalate salt of 2-formyl-11-(3-dimethylaminopropylidene)-6,11-dihydro-5H-pyrrolo[2,1-b][3]-benzazepine is prepared by dissolving the above product in the minimum volume of ethanol and adding dropwise a saturated ethanolic solution of oxalic acid. The resulting crystals are collected by filtration and dried to give 2-formyl-11-(3-dimethylaminopropylidene)-6,11-dihydro-5H-pyrrolo[2,1-b][3]benzazepine oxalate, m.p. 181° C. (decomp.).

Employing 2-cyano-11-(3-dimethylaminopropylidene)-6,11-dihydro-5H-pyrrolo[2,1-b][3]benzazepine as starting material results in the same product.

Employing the procedure substantially as described in Example III, but substituting for the starting material used therein an equimolecular amount of 2-cyano-11-(3-dimethylaminopropyl)-11-hydroxy-11H-pyrrolo[2,1-b][3]benzazepine or 2-cyano-11-(3-dimethylaminopropylidene)-11H-pyrrolo[2,1-b][3]benzazepine, there is produced 2-formyl-11-(3-dimethylaminopropylidene)-11H-pyrrolo[2,1-b][3]benzazepine, which yields a crystalline oxalate salt, m.p. 185° C. (decomp.).

Following the procedure substantially as described in Example III, but substituting for the starting material used therein, an equimolecular amount of 9-cyano-11-(3-dimethylaminopropylidene)-6,11-dihydro-5H-pyrrolo[2,1-b][3]benzazepine or 9-cyano-11-hydroxy-11-(3-dimethylaminopropyl)-6,11-dihydro-5H-pyrrolo[2,1-b][3]benzazepine, there is produced 9-formyl-11-(3-dimethylaminoproplyidene)-6,11-dihydro-5H-pyrrolo[2,1-b][3]benzazepine, which yields a crystalline oxalate salt, m.p. 148°-152° C.(dec.).

Similarly, by substituting 9-cyano-11-(3-dimethylaminopropylidene)-11H-pyrrolo[2,1-b][3]benzazepine or its intermediate carbinol as starting material, there is produced 9-formyl-11-(3-dimethylaminopropylidene)-11H-pyrrolo[2,1-b][3]benzazepine.

EXAMPLE IV

9-Trifluoromethylthio-11-(3-dimethylaminopropylidene)-6,11-dihydro-5H-pyrrolo[2,1-b][3]benzazepine A mixture of 2.9 g. of 9-iodo-11-(3-dimethylaminopropylidene)-6,11-dihydro-5H-pyrrolo[2,1-b][3]benzazepine 5.14 g. of copper (electrolytic dust), 9.0 g. of bis(trifluoromethylthio)mercury and 20 ml. of dimethylformamide was stirred and heated on a steam bath for 5 hours. The mixture was cooled in ice, treated with 75 ml. of benzene and treated dropwise with 50 ml. of 10% sodium hydroxide solution. After 1 hour at room temperature the mixture was filtered through diatomaceous earth followed by a benzene wash. The filtrate was extracted with benzene. The combined benzene fractions were washed with water, dried, filtered and concentrated to dryness to give 9-trifluoromethylthio-11-(3-dimethylaminopropylidene)-6,11-dihydro-5H-pyrrolo[2,1-b][3]benzazepine.

Following the procedure of Example IV, but substituting for the copper dust and the bis(trifluoromethylthio)mercury used therein, an equimolecular amount of cuprous methylsulfide or cuprous isopropylsulfide, there are produced 9-methylthio-11-(3-dimethylaminopropylidene)-6,11-dihydro-5H-pyrrolo[2,1-b][3]benzazepine, and 9-isopropylthio-11-(3-dimethylaminopropylidene)-6,11-dihydro-5H-pyrrolo[2,1-b][3]benzazepine, respectively.

EXAMPLE V

9-Trifluoromethylthio-11-(3-dimethylaminopropylidene)-11H-pyrrolo[2,1-b][3]benzazepine Employing the procedure of Example IV, but substituting for the 9-iodo compound used therein an equimolecular amount of 9-bromo-11-(3-dimethylaminopropylidene)-11H-pyrrolo[2,1-b][3]benzazepine, there is produced 9-trifluoromethylthio-11-(3-dimethylaminopropylidene)-11H-pyrrolo[2,1-b][3]benzazepine.

Employing the procedure of Example V, but substituting for the copper dust and bis(trifluoromethylthio) mercury used therein an equimolecular amount of cuprous methylsulfide or cuprous isopropylsulfide, there is produced respectively:

9-methylthio-11-(3-dimethylaminopropylidene)-11H-pyrrolo[2,1-b][3]benzazepine, and
9-isopropylthio-11-(3-dimethylaminopropylidene)-11H-pyrrolo[2,1-b][3]benzazepine.

EXAMPLE VI

9-Cyano-11-(3-dimethylaminopropylidene)-6,11-dihydro-5H-pyrrolo[2,1-b][3]benzazepine A stirred mixture of 1 gm. of 9-iodo-11-(3-dimethylaminopropylidene)-6,11-dihydro-5H-pyrrolo[2,1-b][3]benzazepine, 1 gm. of cuprous cyanide, and 5 ml. of dimethylformamide is heated to reflux for 5 hr. The mixture is then poured into a solution of 4 gm. of ferric chloride hydrate in 25 ml. of 2 N hydrochloric acid. After stirring the resulting mixture at 60° for 30 min., it is extracted with 3 × 50 ml. of ethyl acetate. The aqueous acidic solution is then basified with sodium hydroxide and extracted with 3 × 50 ml. of ether. The combined ether extracts are then dried and evaporated to yield 9-cyano-11-(3-dimethylaminopropylidene)-6,11-dihydro-5H-pyrrolo[2,1-b][3]benzazepine.

Employing the procedure of Example VI, but substituting for the starting material used therein an equimolecular amount of 9-bromo-11-(3-dimethylaminopropylidene)-11H-pyrrolo[2,1-b][3]benzazepine, there is produced 9-cyano-11-(3-dimethylaminopropylidene)-11H-pyrrolo[2,1-b][3]benzazepine.

EXAMPLE VII

9-Amino-11-(3-dimethylaminopropylidene)-6,11-dihydro-5H-pyrrolo[2,1-b][3]benzazepine A mixture of 9-nitro-11-(3-dimethylaminopropylidene)-6,11-dihydro-5H-pyrrolo[2,1-b][3]benzazepine (2.0 g.), 0.2 g. of 10% Pd/C and 350 ml. of methanol is hydrogenated until the theoretical amount of hydrogen is absorbed. The mixture is filtered and the filtrate is evaporated to dryness to yield 9-amino-11-(3-dimethylaminopropylidene)-6,11-dihydro-5H-pyrrolo[2,1-b][3]benzazepine.

EXAMPLE VIII

9-Ethoxycarbonylamino-11-(3-dimethylaminopropylidene)-11H-pyrrolo[2,1-b][3]benzazepine To 9-carboxy-(3-dimethylaminopropylidene)-11H-pyrrolo[2,1-b][3]benzazepine (123.2 g., 0.4 moles) in 500 ml. ethanol, is added successively triethylamine (52 g., 0.52 moles) and diphenylphosphoroazide (112 g., 0.40 mmoles). Reflux is maintained for 3 hours. The mixture is poured onto water, extracted with ethyl acetate, washed with 1 N sodium hydroxide and dried over magnesium sulfate to yield after evaporation 70 g. of a residue that is chromatographed on silica gel. Elution with methylene chloride yields 9-ethoxycarbonylamino-11-(3-dimethylaminopropylidene)-11H-pyrrolo[2,1-b][3]benzazepine.

EXAMPLE IX

9-Amino-11-(3-dimethylaminopropylidene)-11H-pyrrolo[2,1-b][3]benzazepine

To 9-ethoxycarbonylamino-11-(3-dimethylaminopropylidene)-11H-pyrrolo[2,1-b][3]benzazepine (2.80 g.) in 100 ml. EtOH is added 10 ml. 2 N potassium hydroxide. Reflux is maintained for 42 hours. The volatiles are removed under vacuum and the residue is extracted with chloroform, washed with water, and dried over magnesium sulfate. Evaporation leaves a dark residue that is purified by chromatography on silica gel. Elution with 10% methanol in chloroform yields 9-amino-11-(3-dimethylaminopropylidene)-11H-pyrrolo[2,1-b][3]benzazepine.

EXAMPLE X

9-Methylamino-11-(3-dimethylaminopropylidene)-6,11-dihydro-5H-pyrrolo[2,1-b][3]benzazepine A solution of 9-amino-11-(3-dimethylaminopropylidene)-6,11-dihydro-5H-pyrrolo[2,1-b][3]benzazepine in triethyl orthoformate (2.8 g.; 10 mmoles in 80 ml.) was refluxed for 5 hours. The volatiles were removed under vacuum and the residue dissolved in 100 ml. of absolute ethanol was stirred in an ice bath as sodium borohydride (0.88 g., 0.024 moles) was added over a period of 10 minutes. The mixture was stirred for a period of 2 hours. After concentration of the ethanol, the residue was dissolved in ethyl acetate, washed with water, dried over Na$_2$SO$_4$ and concentrated to dryness to yield 9-methylamino-11-(3-dimethylaminopropylidene)-6,11-dihydro-5H-pyrrolo[2,1-b][3]benzazepine.

Employing the procedure as described in Example X but substituting for the starting material used therein an equimolecular amount of the 9-amino-11-(3-dimethylaminopropylidene)-11H-pyrrolo[2,1-b][3]benzazepine, there is produced 9-methylamino-11-(3-dimethylaminopropylidene)-11H-pyrrolo[2,1-b][3]benzazepine.

EXAMPLE XI

9-Dimethylamino-11-(3-dimethylaminopropylidene)-6,11-dihydro-5H-pyrrolo[2,1-b][3]benzazepine To a solution of 9-amino-11-(3-dimethylaminopropylidene)-6,11-dihydro-5H-pyrrolo[2,1-b][3]benzazepine (2.0 g., 10 mmoles) and 4 ml. (50 mmoles) of 37% aqueous formaldehyde in 15 ml. of acetonitrite is added 1 g. (16 mmoles) of sodium cyano borohydride. A vigorous and exothermic reaction takes place and a dark residue separates. The mixture is stirred for 15 minutes and then glacial acetic acid is added dropwise until the solution tests neutral on wet pH paper. Stirring is maintained for an additional 2 hours. The volatiles are removed under vacuum, and the residue is dissolved in chloroform. The solution is washed with base and with water, dried over sodium sulfate, and concentrated to leave a residue that is purified by chromatography on silica gel. Elution with chloroformmethanol yields 9-dimethylamino-11-(3-dimethylaminopropylidene)-6,11-dihydro-5H-pyrrolo[2,1-b][3]benzazepine.

Employing the procedure of Example XI, but substituting for the starting material used therein an equimolecular amount of 9-amino-11-(3-dimethylaminopropylidene)-11H-pyrrolo[2,1-b][3]benzazepine, there is produced 9-dimethylamino-11-(3-dimethylaminopropylidene)-11H-pyrrolo[2,1-b][3]benzazepine.

EXAMPLE XII

9-Acetamido-11-(3-dimethylaminopropylidene)-11H-pyrrolo[2,1-b][3]benzazepine 9-Amino-11-(3-dimethylaminopropylidene)-11H-pyrrolo[2,1-b][3]benzazepine (11.4 mmoles) dissolved in 15 ml. pyridine is treated with acetic anhydride (2 ml.) at room temperature for 19 hours. The volatiles are removed under vacuum and the residue is dissolved in chloroform, and chromatographed on silica gel. Elution with chloroform-methanol yields 9-acetamido-11-(3-dimethylaminopropylidene)-11H-pyrrolo[2,1-b][3]benzazepine.

Employing the procedure of Example XII but substituting for the starting material used therein, an equimolecular amount of 9-amino-11-(3-dimethylaminopropylidene)-6,11-dihydro-5H-pyrrolo[2,1-b][3]benzazepine, there is produced 9-acetamido-11-(3-dimethylaminopropylidene)-6,11-dihydro-5H-pyrrolo[2,1-b][3]benzazepine.

EXAMPLE XIII

2-Dimethylcarbamoyl-11-(3-dimethylaminopropylidene)-11H-pyrrolo[2,1-b][3]benzazepine Step A: Preparation of 2-carbamoyl-11-(3-dimethylaminopropylidene)-11H-pyrrolo[2,1-b][3]benzazepine 2-Cyano-11-(3-dimethylaminopropylidene)-11H-pyrrolo[2,1-b][3]benzazepine (0.135 mole) in 100 ml. of concentrated hydrochloric acid and 100 ml. of acetic acid is refluxed for 2 hours. It is then poured onto 500 ml. of water and continuously extracted with methylene chloride. The solution is left to cool to room temperature and filtered to afford 2-carbamoyl-11-(3-dimethylaminopropylidene)-11H-pyrrolo[2,1-b][3]benzazepine.

Step B: Preparation of 2-carboxy-11-(3-dimethylaminopropylidene)-11H-pyrrolo[2,1-b][3]benzazepine To 2-carbamoyl-11-(3-dimethylaminopropylidene)-11H-pyrrolo[2,1-b][3]benzazepine (0.112 moles) in 300 ml. of 50% sulfuric acid maintained at 50° C. is added slowly 25 g. of sodium nitrite in 75 ml. of water. At the end of the addition, the solid is filtered, washed with water and air-dried to yield 2-carboxy-11-(3-dimethylaminopropylidene)-11H-pyrrolo[2,1-b][3]benzazepine.

Step C: Preparation of 2-chlorocarbonyl-11-(3-dimethylaminopropylidene)-11H-pyrrolo[2,1-b][3]benzazepine 2-Carboxy-11-(3-dimethylaminopropylidene)-11H-pyrrolo[2,1-b][3]benzazepine (99 mmoles) in 100 ml. of thionyl chloride is refluxed for 15 minutes. The volatiles are removed under vacuum and the residue is triturated in ether. Filtration and air drying yields 2-chlorocarbonyl-11-(3-dimethylaminopropylidene)-11H-pyrrolo[2,1-b][3]benzazepine.

Step D: Preparation of 2-dimethylcarbamoyl-11-(3-dimethylaminopropylidene)-11H-pyrrolo[2,1-b][3]benzazepine Anhydrous dimethyl amine is bubbled through a suspension of 2-chlorocarbonyl-11-(3-dimethylaminopropylidene)-11H-pyrrolo[2,1-b][3]benzazepine (88.5 mmoles) in 100 ml. of methylene chloride. (Note: The introduction of dimethyl amine causes the mixture to reflux and this reflux stops when all the acid chloride is reacted.)

The reaction mixture is washed with water and dried over sodium sulfate. It is then taken to dryness, triturated in ether, filtered and air-dried to yield 2-dimethylcarbamoyl-11-(3-dimethylaminopropylidene)-11H-pyrrolo[2,1-b][3]benzazepine.

Following the procedure of Example XIII, Step D, but substituting for the dimethylamine used therein, an equimolecular amount of methylamine, there is produced 2-methylcarbamoyl-11-(3-dimethylaminopropylidene)-11H-pyrrolo[2,1-b][3]benzazepine.

EXAMPLE XIV

2-Methoxycarbonyl-11-(3-dimethylaminopropylidene)-11H-pyrrolo[2,1-b][3]benzazepine 2-Carboxy-11-(3-dimethylaminopropylidene)-11H-pyrrolo[2,1-b][3]benzazepine (0.11 moles) in 300 ml. of methanol saturated with hydrogen chloride is refluxed until a homogeneous solution is obtained (4 hours.).

The volatiles are removed under vacuum and the residue is dissolved in 300 ml. of methylene chloride, washed with dilute sodium hydroxide and then with water. The organic solution is dried over sodium sulfate and evaporated to yield 2-methoxycarbonyl-11-(3-dimethylaminopropylidene)-11H-pyrrolo[2,1-b][3]benzazepine.

EXAMPLE XV

2-Cyano-6,11-dihydro-11-(3-methylaminopropylidene)-5H-pyrrolo[2,1-b][3]benzazepine oxalate salt Step A: Preparation of 2-cyano-6,11-dihydro-11-(N-2,2,2-trichloroethoxycarbonyl-3-methylaminopropylidene)-5H-pyrrolo[2,1-b][3]benzazepine 2-Cyano-6,11-dihydro-11-(3-dimethylaminopropylidene)-5H-pyrrolo[2,1-b][3]benzazepine (5 g., 17.2 mmoles) and 2,2,2-trichloroethylchloroformate (4 g., 18.8 mmoles) in 100 ml. benzene were refluxed for 18 hours. The mixture was poured onto water, washed with dilute hydrochloric acid and then with water, dried over sodium sulfate and concentrated under vacuum to yield 7.1 g. of dark red oil. It was adsorbed on 250 g. silica gel and eluted with 2 liters benzene. The eluate was discarded.

Elution with 1.2 liters of methylene chloride left, after evaporation, 2-cyano-6,11-dihydro-11-(N-2,2,2-trichloroethoxy-carbonyl-3-methylaminopropylidene)-5H-pyrrolo[2,1-b][3]benzazepine as a brown oil (5.0 g., 63%), $R_f$ 0.6 (benzene-ethyl acetate 3:1, on silica gel TLC).

Step B: Preparation of 2-cyano-6,11-dihydro-11-(methylaminopropylidene)-5H-pyrrolo[2,1-b][3]benzazepine.oxalate salt 2-Cyano-6,11-dihydro-11-(N-2,2,2-trichloroethoxycarbonyl-3-methylaminopropylidene)-5H-pyrrolo[2,1-b][3]benzazepine (4.0 g., 8.7 mmole) and zinc dust (8 g.) in 25 ml. acetic acid was stirred at room temperature for 18 hours. The solid was filtered off and washed with acetic acid. The filtrate was taken to dryness. The residue was dissolved in dilute hydrochloric acid and extracted with ethyl acetate. The aqueous phase was then made basic, extracted with methylene chloride; the organic layer was washed with water, dried over sodium sulfate and concentrated to yield 2-cyano-6,11-dihydro-11-(methylaminopropylidene)-5H-pyrrolo[2,1-b][3]benzazepine (2.3 g., 95%) as a brown oil.

This oil was dissolved in 25 ml. ethanol and treated with oxalic acid (1 g.). The oxalate salt was filtered, washed with ethanol and air-dried. The yield was 2.54 g., m.p. 190° C. (dec.).

Employing the procedure of Example XV, Steps A and B, but substituting for the 2-cyano-6,11-dihydro-11-(3-dimethylaminopropylidene)-5H-pyrrolo[2,1-b][3]benzazepine used in Step A thereof, an equimolecular amount of any of the 11-(3-dialkylaminopropylidene)pyrrolo[2,1-b][3]benzazepines described in Tables A and B and Examples I through XIV, there are produced the corresponding 11-(3-alkylaminopropylidene)pyrrolo[2,1-b][3]benzazepines such as those depicted in Table C by the following process:

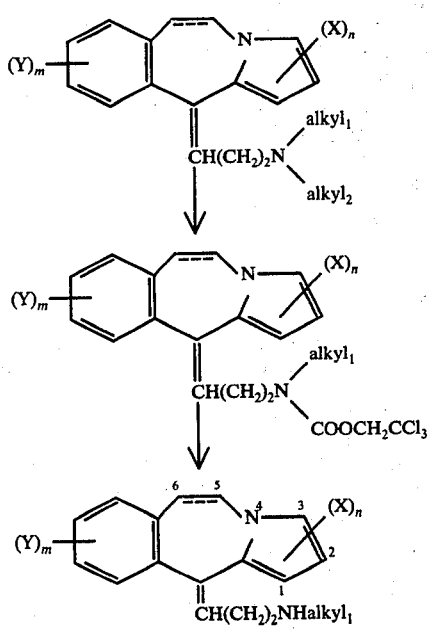

TABLE C

| 6-5 Positions | $(Y)_m$ | $(X)_n$ | alkyl$_1$ | alkyl$_2$ |
|---|---|---|---|---|
| unsaturated | H | 2-CN | CH$_3$ | CH$_3$ |
| saturated | H | 2-CHO | CH$_3$ | CH$_3$ |
| unsaturated | H | 2-CHO | CH$_3$ | CH$_3$ |
| saturated | H | 2-CO(CH$_2$)$_4$H | CH$_3$ | CH$_3$ |
| unsaturated | H | 2-CO(CH$_2$)$_4$H | CH$_3$ | CH$_3$ |
| saturated | H | H | CH$_3$ | CH$_3$ |
| unsaturated | H | H | CH$_3$ | CH$_3$ |
| saturated | 9-CN | H | CH$_3$ | CH$_3$ |
| unsaturated | 9-CN | H | CH$_3$ | CH$_3$ |
| unsaturated | 9-CHO | H | CH$_3$ | CH$_3$ |
| saturated | 9-CHO | H | CH$_3$ | CH$_3$ |
| saturated | H | 2-CN | C$_2$H$_5$ | CH$_3$ |
| unsaturated | H | 2-CN | C$_2$H$_5$ | CH$_3$ |
| saturated | H | 2-CN | ◁ | CH$_3$ |
| saturated | H | 2-CN | —CH$_2$CH=CH$_2$ | —CH$_2$CH=CH$_2$ |

EXAMPLE XVI

Separation of the isomers of 11-(3-dimethylaminopropylidene)-6,11-dihydro-5H-pyrrolo[2,1-b][3]benzazepine To a solution of 24 g. (0.0775 moles) of 11-hydroxy-11-(3-dimethylaminopropyl)-6,11-dihydro-5H-pyrrolo[2,1-b][3]benzazepine in 35 ml. of ethanol was added a solution of 7.8 g. (0.086 moles) of oxalic acid in 90 ml. of ethanol at 25° C. over 20 minutes. The mixture was then stirred for 16 hours at 25° C. and the insoluble oxalate salt removed by filtration to yield 22.7 g. (0.064 moles) of crude oxalate of isomer I. Recrystallization from 150 ml. of hot water gave 15.4 g. of isomer I oxalate, m.p. 188°–189° C., unchanged by further recrystallization.

The filtrate from crude isomer I was worked up by basification to yield 4.18 g. (0.016 moles) of crude isomer II as the free base. To a solution of this crude free base in 80 ml. of methanol was added 1.41 g. (0.016 moles) oxalic acid, and the resulting solution was treated with charcoal at reflux for 5 minutes. The solution was filtered, evaporated and the residual oil taken up in 100 ml. of acetonitrile and treated with charcoal at reflux for 5 minutes. This charcoal treatment was repeated twice more, and the solution evaporated to leave a semi-solid which was dissolved in 100 ml. of methanol. The methanol solution was evaporated and the resulting oil dissolved in 20 ml. of acetonitrile, seeded and held at 5° C. The resulting crystals were pulverized, filtered, washed with acetonitrile and finally with ether to give 2.68 gm. (0.0075 moles) of isomer II oxalate, m.p. 110°–120° C.

Each isomer was shown to be at least 90% pure by nmr analysis.

EXAMPLE XVII

Chromatographic separation of the geometrical isomers of 2-formyl-6,11-dihydro-11-(3-dimethylaminopropylidene)-5H-pyrrolo[2,1-b][3]benzazepine 2-Formyl-6,11-dihydro-11-(3-dimethylaminopropylidene)-5H-pyrrolo[2,1-b][3]benzazepine (3.2 g.) was absorbed on 300 g. silica gel and elution was carried out using 2% methanol in chloroform with fractions of 10 ml. The first isomer came out between tubes (fractions) 70 and 109; evaporation of the eluent from these fractions yielded 0.8 g. of an oil which solidified on standing. This was isomer I, m.p. 104°–105° C., which gave a crystalline oxalate salt, m.p. 198°–200° C.(dec.). Between tubes 110 and 159, a mixture of the two isomers was obtained (1.62 g.) and finally 0.49 g. of isomer II was obtained by evaporating to dryness tubes 160 to 210. A crystalline oxalate salt of isomer II was obtained with m.p. 204°–206° C.(dec.).

The difference between the two isomers was best seen by nmr. For the isomer I, the formyl proton absorbed at 9.56 ppm and the N—(CH$_3$)$_2$ protons at 2.10 ppm; for the isomer II, the formyl proton was at 9.61 ppm and the N—(CH$_3$)$_2$ protons were at 2.20 ppm.

EXAMPLE XVIII

Chromatographic separation of the geometric isomers of 9-chloro-11-(3-dimethylaminopropylidene)-6,11-dihydro-5H-pyrrolo[2,1-b][3]benzazepine A mixture of the geometric isomers (7.6 g., 25.3 mmoles) of 9-chloro-11-(3-dimethylaminopropylidene)-6,11-dihydro-5H-pyrrolo[2,1-b][3]benzazepine was chromatographed over 1.4 kg. of silica gel (75–250 microns) using 3% (v/v) methanol in chloroform as eluant and collecting fractions of 80 ml. each:

(a) Fractions 1–6: 3.4 g. of (E)-isomer
(b) Fractions 7–20: 3.0 g. of isomer mixture.
(c) Fractions 21–24: 1.3 g. of (Z)-isomer.

Fraction (b) was rechromatographed on 600 g. of silica gel in the same manner to give:

(d) Fraction 1: 0.92 g. of (E)-isomer
(e) Fractions 2–3: 0.82 g. of isomer mixture.
(f) Fractions 4–6: 0.65 g. of isomer mixture
(g) Fractions 7–12: 0.73 g. of (Z)-isomer.

Combined fractions (a) and (d) were rechromatographed over 900 gm. of silica gel by eluting with 2% (v/v) methanol in chloroform at 3 ml./min. to give 3.4 g. of (E)-isomer (>99.9% pure) as a light yellow oil. The hydrogen maleate salt has m.p. 134°–135° C.

Combined fractions (c) and (g) were rechromatographed over 800 g. of silica gel by elution with 3% (v/v) methanol in chloroform at 3 ml./min. to give 0.4 g. of (Z)-isomer (>99.9% pure). The hydrogen maleate salt has m.p. 138°–139° C.

EXAMPLE XIX

Separation of geometric isomers of 9-chloro-11-(3-dimethylaminopropylidene)-11H-pyrrolo[2,1-b][3]benzazepine A mixture of the geometric isomers (26 gm., 87 moles) of 9-chloro-11-(3-dimethylaminopropylidene)-11H-pyrrolo[2,1-b][3]benzazepine was chromatographed over 1500 g. of silica gel (75–250 microns) by elution with 2% (v/v) methanol in chloroform to give:

(a) Fraction 1: 2.4 g. of (E)-isomer (>99.9% pure)
(b) Fraction 2: 9.0 g. of isomer mixture (50/50)
(c) Fraction 3: 2.26 g. of isomer mixture (16% (E)/84%(Z))
(d) Fraction 4: 4.4 g. of (Z)-isomer (98–99% pure)
(e) Fraction 5: 5.6 g. of (Z)-isomer (>99.9% pure)

Fraction (b) was rechromatographed on 900 gm. of silica gel to give
(f) Fraction 1: 2.55 g. of (E)-isomer (>99.9% pure)
(g) Fraction 2: 2.7 g. of isomer mixture
(h) Fraction 3: 2.0 g. of (Z)-isomer (>99.9% pure)

Fraction (f) crystallized on standing and 300 mg. was recrystallized from 2 ml. of hexane to give 110 mg. of crystalline free base of (E)-9-chloro-11-(3-dimethylaminopropylidene)-11H-pyrrolo[2,1-b][3]benzazepine, m.p. 75° C. The hydrogen maleate salt has m.p. 117°–118° C.

The hydrogen maleate salt of (Z)-9-chloro-11-(3-dimethylaminopropylidene)-11H-pyrrolo[2,1-b][3]benzazepine has m.p. 130°–132° C.

Following the procedure substantially as described in Example XVII, XVIII or XIX but substituting for the compounds employed therein an equimolecular amount of any of the pyrrolo[2,1-b][3]benzazepines described in Examples I through XV and XXII, and Tables A, B, and C, there are produced the corresponding geometric isomers.

EXAMPLE XX

2-Cyano-6,11-dihydro-11-(3-dimethylaminopropylidene)-5H-pyrrolo[2,1-b][3]benzazepine, oxalate salt; isomer I 2-Formyl-6,11-dihydro-11-(3-dimethylaminopropylidene)-5H-pyrrolo[2,1-b][3]benzazepine (Isomer I from Example XVII) (1.4 g., 4.8 mmoles), hydroxylamine hydrochloride (0.7 g., 10 mmoles) and sodium formate (0.85 g., 12.5 mmoles) in 20 ml. ethanol were heated on a steam-bath for 5 minutes. The volatiles were removed under vacuum; 5% sodium bicarbonate was added to the residue and the solution was extracted with methylene chloride. The organic phase was washed with water, dried over sodium sulfate and concentrated to yield 1.4 g. of oxime.

The oxime in 10 ml. trichloroacetonitrile was heated on a steam-bath for 15 minutes. The solution was taken to dryness under vacuum, water was added, and the resulting mixture was extracted with methylene chloride to yield after usual washings and drying 1.9 g. of crude 2-cyano-6,11-dihydro-11-(3-dimethylaminopropylidene)-5H-pyrrolo[2,1-b][3]benzazepine as a brown oil.

It was adsorbed on 100 g. silica gel and eluted with chloroform to yield trichloroacetamide which was discarded. Elution with 10% methanol in chloroform yielded pure 2-cyano-6,11-dihydro-11-(3-dimethylaminopropylidene)-5H-pyrrolo[2,1-b][3]benzazepine as a brown oil (0.84 g., 60%).

Dissolved in 5 ml. of ethanol and treated with 300 mg. of oxalic acid in 0.5 ml. ethanol, the free base yielded the oxalate salt (0.85 g., 45%), m.p. 217° C. (dec.).

EXAMPLE XXI

2-Cyano-6,11-dihydro-11-(3-dimethylaminopropylidene)-5H-pyrrolo[2,1-b][3]benzazepine, oxalate salt; Isomer II Employing the procedure of Example XX but starting with Isomer II of the 2-formyl derivative from Example XVII, there was produced 2-cyano-6,11-dihydro-11-(3-dimethylaminopropylidene)-5H-pyrrolo[2,1-b][3]benzazepine, oxalate salt; Isomer II, m.p. 223° C. (dec.).

EXAMPLE XXII

2-Formyl-11-(3-dimethylaminopropylidene)-6,11-dihydro-5H-pyrrolo[2,1-b][3]benzazepine Step A: Preparation of 6,11-dihydro-2-(2-dioxolanyl)-5H-pyrrolo[2,1-b][3]benzazepin-11-one A mixture of 5 gm. of 6,11-dihydro-2-formyl-5H-pyrrolo[2,1-b][3]benzazepin-11-one, 2.5 gm. of ethylene glycol, 0.5 gm. of p-toluenesulfonic acid and 100 ml. of toluene is refluxed for 16 hr. in an apparatus designed to remove water formed during the reaction (Dean-Stark apparatus). The reaction mixture is cooled to 0° C. and washed rapidly with ice cold 5% sodium carbonate solution (2 × 50 ml.) and dried over $Na_2SO_4$. Evaporation of the solvent leaves 6,11-dihydro-2-(2-dioxolanyl)-5H-pyrrolo[2,1-b][3]benzazepin-11-one as an oil which is of sufficient purity for use in the next step.

Step B: Preparation of 6,11-dihydro-2-(2-dioxolanyl)-11-hydroxy-11-(3-dimethylaminopropyl)-5H-pyrrolo[2,1-b][3]benzazepine Employing substantially the procedure of Example I, Step A, but using the ketone acetal from Step A of the present example, there is obtained 6,11-dihydro-2-(2-dioxolanyl)-11-hydroxy-11-(3-dimethylaminopropyl)-5H-pyrrolo[2,1-b][3]benzazepine.

Step C: Preparation of 2-formyl-11-(3-dimethylaminopropylidene)-6,11-dihydro-5H-pyrrolo[2,1-b][3]benzazepine To a solution of 3 gm. of 6,11-dihydro-2-(2-dioxolanyl)-11-hydroxy-11-(3-dimethylaminopropyl)-5H-pyrrolo[2,1-b][3]benzazepine in 20 ml. of ethanol containing 1 ml. of water is added 2 gm. of oxalic acid, and the resulting mixture heated to reflux for 2 hr. Upon cooling to 0° C. for 4 hr., there is obtained the crystalline oxalate of 2-formyl-11-(3-dimethylaminopropylidene)-6,11-dihydro-5H-pyrrolo[2,1-b][3]benzazepine, m.p. 181° C. (decomp.).

Using substantially the same procedure as in Example XXII, Steps A, B, and C (the present example) but starting with 2-formyl-11H-pyrrolo[2,1-b][3]benzazepin-11-one, 6,11-dihydro-9-formyl-5H-pyrrolo[2,1-b][3]benzazepin-11-one, or 9-formyl-11H-pyrrolo[2,1-b][3]benzazepin-11-one, there is obtained 2-formyl-11-(3-dimethylaminopropylidene)-11H-pyrrolo[2,1-b][3]benzazepine, 9-formyl-11-(3-dimethylaminopropylidene)-6,11-dihydro-5H-pyrrolo[2,1-b][3]benzazepine, or 9-formyl-11-(3-dimethylaminopropylidene)-11H-pyrrolo[2,1-b][3]benzazepine, respectively.

EXAMPLE XXIII

9-Chloro-11-(3-aminopropylidene)-11H-pyrrolo[2,1-b][3]benzazepine

Anhydrous 3-aminopropyltriphenylphosphonium bromide hydrobromide, 9.0 g., is suspended in 30 ml. dry tetrahydrofuran and 0.038 moles of butyl lithium in heptane is added during 1 hour. After an additional 30 minutes, 3.44 g. of 9-chloro-11H-pyrrolo[2,1-b][3]benzazepin-11-one is added to the deep red solution and the reaction is maintained at reflux for 10 hours. Water, 500 ml., is added at room temperature and the solvent is removed in vacuo. The crude residue is treated with 10% hydrochloric acid until acidic (pH 2) and then 100 ml. benzene is added. After stirring, the benzene layer is removed by decantation and the remaining mixture is rendered basic with 10% sodium hydroxide solution and is extracted with 3 × 50 ml. portions of benzene. The benzene extracts are washed, then dried with anhydrous sodium sulfate and concentrated in a vacuum leaving a residue of 9-chloro-11-(3-aminopropylidene)-11H-pyrrolo[2,1-b][3]benzazepine.

Following the procedure substantially as described in Example XXIII, but substituting for the ketone used therein, the ketones described in Table D, there are produced the 3-($R^1$,$R^2$-aminopropylidene)pyrrolo[2,1-b][3]benzazepines also described in Table D, according to the following process wherein $X_a$, $Y_a$, $n$, $m$, $R^1$, $R^2$ and the dotted line are as previously defined.

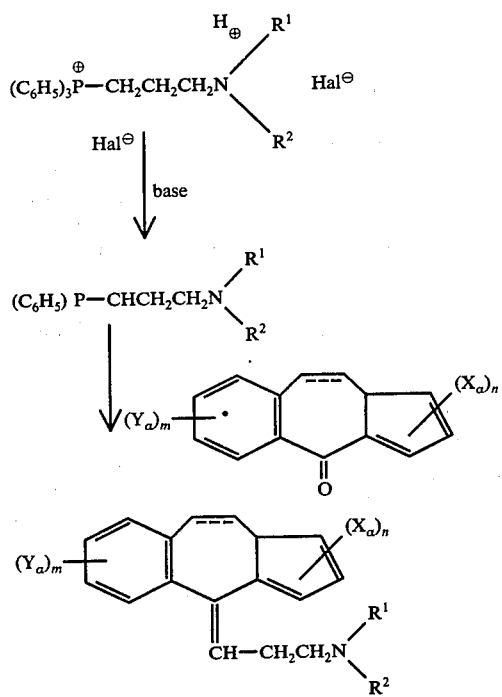

TABLE D

| $R^1$ | $R^2$ | $(Y_a)_m$ | $(X_a)_n$ | 5,6-position |
|---|---|---|---|---|
| H | H | H | H | saturated |
| CH₃ | CH₃ | H | 2-CN | saturated |
| CH₃ | CH₃ | H | H | saturated |
| CH₃ | H | H | H | saturated |
| CH₃ | CH₃ | 9-SCH₃ | H | saturated |
| CH₃ | CH₃ | 9-I | H | saturated |
| CH₃ | CH₃ | 9-CN | H | saturated |
| CH₃ | CH₃ | 9-SO₂CH(CH₃)₂ | H | saturated |
| CH₃ | CH₃ | 9-Cl | H | saturated |
| CH₃ | H | 9-Cl | H | saturated |
| C₂H₅ | CH₃ | 9-Cl | H | saturated |
| H | H | 9-Cl | H | saturated |
| CH₃ | CH₃ | H | H | unsaturated |
| CH₃ | CH₃ | 9-Cl | H | unsaturated |
| CH₃ | H | 9-Cl | H | unsaturated |
| C₂H₅ | CH₃ | 9-Cl | H | unsaturated |
| CH₃ | CH₃ | H | 2-COCH(CH₃)₂ | unsaturated |
| CH₃ | CH₃ | 9-Br | H | unsaturated |
| CH₃ | CH₃ | H | 2-CF₃ | unsaturated |
| CH₃ | H | H | H | unsaturated |
| H | H | H | H | unsaturated |

EXAMPLE XXIV
Pharmaceutical Compositions

A typical tablet containing 5 mg. (E)-9-chloro-11-(3-dimethylaminopropylidene)-11H-pyrrolo[2,1-b][3]benzazepine hydrogen maleate per tablet is prepared by mixing together with the active ingredient calcium phosphate, lactose and starch in the amounts shown in the tables below. After these ingredients are thoroughly mixed, the dry mixture is blended for an additional three minutes. This mixture is then compressed into tablets weighing approximately 129 mg. each. Similarly prepared are tablets containing (E)-9-chloro-11-(3-dimethylaminopropylidene)-6,11-dihydro-5H-pyrrolo[2,1-b][3]benzazepine, 11-(3-dimethylaminopropylidene)-6,11-dihydro-5H-pyrrolo[2,1-b][3]benzazepine, or any of the other novel compounds of this invention.

Tablet Formula

| Ingredient | Mg. per Tablet |
|---|---|
| (E)-9-chloro-11-(3-dimethylaminpropylidene)-11H-pyrrolo-[2,1-b][3]-benzazepine hydrogen maleate | 5 mg. |
| Calcium phosphate | 52 mg. |
| Lactose | 60 mg. |
| Starch | 10 mg. |
| Magnesium stearate | 1 mg. |

What is claimed is:
1. A compound of structural formula:

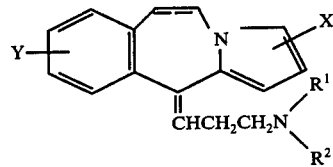

or pharmaceutically acceptable salt thereof, wherein the dotted line represents saturation or unsaturation; X and Y are independently selected from
(1) hydrogen
(2) halo,
(3) formyl,
(4) $C_{2-6}$-alkanoyl,
(5) $C_{1-5}$-alkyl,
(6) ($C_{1-5}$-alkoxy)carbonyl,
(7) hydroxy-$C_{1-3}$-alkyl,
(8) trifluoromethyl
(9) $C_{1-3}$-alkoxy
(10) cyano,
(11) trifluoromethylthio,
(12) $C_{1-3}$-alkylthio,
(13) $C_{1-3}$-alkylsulfonyl,
(14) trifluoromethylsulfonyl,
(15) $C_{1-3}$-alkylsulfinyl,
(16) trifluoromethylsulfinyl,
(17) amino,
(18) $C_{2-6}$-alkanoylamino,
(19) $C_{1-3}$-alkylamino,
(20) di($C_{1-3}$ alkyl)amino,
(21) hydroxy,
(22) N-$C_{1-3}$-alkylcarbamoyl,
(23) N,N-di($C_{1-3}$ alkyl)carbamoyl,
(24) nitro,
(25) di($C_{1-3}$ alkyl)sulfamoyl,
(26) $C_{1-3}$ alkoxycarbonylamino, and

(27) N-C$_{1-3}$ alkylcarbamoyloxy; and R$^1$ and R$^2$ are independently selected from
(1) hydrogen,
(2) C$_{1-3}$-alkyl,
(3) C$_{2-5}$ alkenyl, and
(4) C$_{3-6}$-cycloalkyl, or R$^1$ and R$^2$ joined together form with the nitrogen to which they are attached 1-piperidyl, 1-pyrrolidyl, or 4-morpholinyl.

2. The compound of claim 1 wherein one of X and Y is hydrogen, and the other is hydrogen, cyano, formyl, C$_{2-6}$ alkanoyl, or chloro.

3. The compound of claim 2 wherein X is hydrogen, Y is 9-chloro and R$^1$ and R$^2$ are methyl.

4. The compound of claim 3 which is (E)-9-chloro-11-(3-dimethylaminopropylidene)-6,11-dihydro-5H-pyrrolo[2,1-b][3]benzazepine or a pharmaceutically acceptable salt thereof.

5. The compound of claim 3 which is (E)-9-chloro-11-(3-dimethylaminopropylidene)-11H-pyrrolo[2,1-b][3]benzazepine or a pharmaceutically acceptable salt thereof.

6. A compound of structural formula:

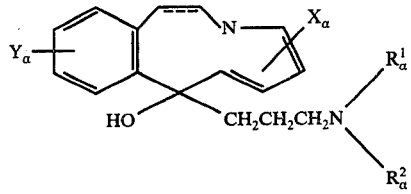

wherein the dotted line represents unsaturation or saturation; X$_\alpha$ and Y$_\alpha$ are independently selected from
(1) hydrogen,
(2) halo,
(3) C$_{2-6}$-alkanoyl,
(4) C$_{1-5}$-alkyl,
(5) (C$_{1-5}$-alkoxy)carbonyl,
(6) hydroxy-C$_{1-3}$-alkyl,
(7) trifluoromethyl
(8) C$_{1-3}$-alkoxy,
(9) cyano,
(10) trifluoromethylthio,
(11) C$_{1-3}$-alkylthio,
(12) C$_{1-3}$-alkylsulfonyl,
(13) trifluoromethylsulfonyl,
(14) C$_{1-3}$-alkylsulfinyl,
(15) trifluoromethylsulfinyl,
(16) amino,
(17) C$_{2-6}$-alkanoylamino,
(18) C$_{1-3}$-alkylamino,
(19) di(C$_{1-3}$-alkyl)amino,
(20) hydroxy,
(21) N-C$_{1-3}$-alkylcarbamoyl,
(22) N,N-di(C$_{1-3}$-alkyl)carbamoyl,
(23) nitro,
(24) di(C$_{1-3}$-alkyl)sulfamoyl,
(25) C$_{1-3}$-alkoxycarbonylamino, and
(26) N-C$_{1-3}$-alkylcarbamoyloxy; and R$_\alpha^1$ and R$_\alpha^2$ are independently selected from
(1) C$_{1-3}$-alkyl,
(2) C$_{2-5}$-alkenyl, and
(3) C$_{3-6}$-cycloalkyl, or R$_\alpha^1$ and R$_\alpha^2$ together represent 1-piperidyl, 1-pyrrolidyl or 4-morpholinyl.

7. The compound of claim 6 wherein one of X$_\alpha$ and Y$_\alpha$ is hydrogen, and the other is hydrogen, cyano, C$_{2-6}$ alkanoyl or chloro.

8. The compound of claim 6 wherein X$_\alpha$ is hydrogen, Y$_\alpha$ is 9-chloro, and R$_\alpha^1$ and R$_\alpha^2$ are methyl.

9. A pharmaceutical composition for producing a skeletal muscle relaxing or tranquilizing effect comprising a pharmaceutical carrier and an effective amount of a compound of formula:

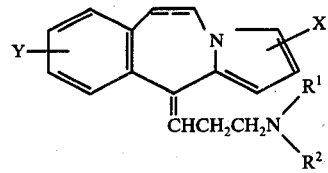

or pharmaceutically acceptable salt thereof wherein the dotted line represents saturation or unsaturation; X and Y are independently selected from
(1) hydrogen
(2) halo,
(3) formyl,
(4) C$_{2-6}$-alkanoyl,
(5) C$_{1-5}$-alkyl,
(6) (C$_{1-5}$-alkoxy)carbonyl,
(7) hydroxy-C$_{1-3}$alkyl,
(8) trifluoromethyl
(9) C$_{1-3}$-alkoxy,
(10) cyano,
(11) trifluoromethylthio,
(12) C$_{1-3}$-alkylthio,
(13) C$_{1-3}$-alkylsulfonyl,
(14) trifluoromethylsulfonyl,
(15) C$_{1-3}$-alkylsulfinyl,
(16) trifluoromethylsulfinyl,
(17) amino,
(18) C$_{2-6}$-alkanoylamino,
(19) C$_{1-3}$-alkylamino,
(20) di(C$_{1-3}$-alkyl)amino,
(21) hydroxy,
(22) N-C$_{1-3}$-alkylcarbamoyl,
(23) N,N-di(C$_{1-3}$-alkyl)carbamoyl,
(24) nitro,
(25) di(C$_{1-3}$-alkyl)sulfamoyl,
(26) C$_{1-3}$-alkoxycarbonylamino, and
(27) N-C$_{1-3}$-alkylcarbamoyloxy; and R$^1$ and R$^2$ are independently selected from
(1) hydrogen,
(2) C$_{1-3}$-alkyl,
(3) C$_{2-5}$-alkenyl, and
(4) C$_{3-6}$-cycloalkyl, or R$^1$ and R$^2$ joined together form with the nitrogen to which they are attached 1-piperidyl, 1-pyrrolidyl, or 4-morpholinyl.

10. The pharmaceutical composition of claim 9, wherein X is hydrogen, Y is 9-chloro and R$^1$ and R$^2$ are methyl.

11. The composition of claim 10 wherein the compound is (E)-9-chloro-11-(3-dimethylaminopropylidene)-6,11-dihydro-5H-pyrrolo[2,1-b][3]-benzazepine or a pharmaceutically acceptable salt thereof.

12. The composition of claim 10 wherein the compound is (E)-9-chloro-11-(3-dimethylaminopropylidene)-11H-pyrrolo[2,1-b][3]benzazepine or pharmaceutically acceptable salt thereof.

13. A method of producing a skeletal muscle relaxant or tranquilizing effect in a patient in need of such treatment comprising the administration of an effective amount of a compound of formula:

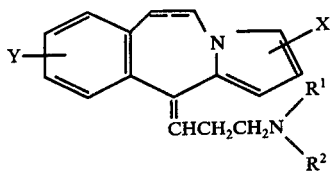

or pharmaceutically acceptable salt thereof, wherein the dotted line represents saturation or unsaturation; X and Y are independently selected from
(1) hydrogen
(2) halo,
(3) formyl,
(4) $C_{2-6}$-alkanoyl,
(5) $C_{1-5}$-alkyl,
(6) ($C_{1-5}$-alkoxy)carbonyl,
(7) hydroxy-$C_{1-3}$-alkyl,
(8) trifluoromethyl
(9) $C_{1-3}$-alkoxy
(10) cyano,
(11) trifluoromethylthio,
(12) $C_{1-3}$-alkylthio,
(13) $C_{1-3}$-alkylsulfonyl,
(14) trifluoromethylsulfonyl,
(15) $C_{1-3}$-alkylsulfinyl,
(16) trifluoromethylsulfinyl,
(17) amino,
(18) $C_{2-6}$-alkanoylamino,
(19) $C_{1-3}$-alkylamino,
(20) di($C_{1-3}$-alkyl)amino,
(21) hydroxy,
(22) N-$C_{1-3}$-alkylcarbamoyl,
(23) N,N-di($C_{1-3}$-alkyl)carbamoyl,
(24) nitro,
(25) di($C_{1-3}$-alkyl)sulfamoyl,
(26) $C_{1-3}$-alkoxycarbonylamino, and
(27) N-$C_{1-3}$-alkylcarbamoyloxy; and
$R^1$ and $R^2$ are independently selected from
(1) hydrogen,
(2) $C_{1-3}$-alkyl,
(3) $C_{2-5}$-alkenyl, and
(4) $C_{3-6}$-cycloalkyl, or
$R^1$ and $R^2$ joined together form with the nitrogen to which they are attached 1-piperidyl, 1-pyrrolidyl, or 4-morpholinyl.

14. The method of claim 13 wherein X is hydrogen, Y is 9-chloro and $R^1$ and $R^2$ are methyl.

15. The method of claim 14 wherein the compound is (E)-9-chloro-11-(3-dimethylaminopropylidene)-6,11-dihydro-5H-pyrrolo[2,1-b][3]benzazepine or a pharmaceutically acceptable salt thereof.

16. The method of claim 14 wherein the compound is (E)-9-chloro-11-(3-dimethylaminopropylidene)-11H-pyrrolo[2,1-b][3]benzazepine or pharmaceutically acceptable salt thereof.